United States Patent
Seibel

(10) Patent No.: US 6,975,898 B2
(45) Date of Patent: Dec. 13, 2005

(54) MEDICAL IMAGING, DIAGNOSIS, AND THERAPY USING A SCANNING SINGLE OPTICAL FIBER SYSTEM

(75) Inventor: Eric J. Seibel, Seattle, WA (US)

(73) Assignee: University of Washington, Seattle, WA (US)

( * ) Notice: Subject to any disclaimer, the term of this patent is extended or adjusted under 35 U.S.C. 154(b) by 792 days.

(21) Appl. No.: 09/850,594

(22) Filed: May 7, 2001

(65) Prior Publication Data

US 2001/0055462 A1 Dec. 27, 2001

Related U.S. Application Data

(60) Provisional application No. 60/212,411, filed on Jun. 19, 2000.

(51) Int. Cl.[7] .................................................. A61B 6/00
(52) U.S. Cl. .................... 600/473; 600/476; 600/478
(58) Field of Search .............................. 600/473, 476, 600/478, 160, 166, 178, 181, 182; 607/89, 92; 385/117, 118, 130, 147; 356/301, 319, 320, 326; 250/208.1, 458.1, 459.1, 461.1, 461.2

(56) References Cited

U.S. PATENT DOCUMENTS

| | | | |
|---|---|---|---|
| 4,410,235 A | 10/1983 | Klement et al. | 350/96.18 |
| 4,768,513 A * | 9/1988 | Suzuki | |
| 5,074,642 A | 12/1991 | Hicks | 385/116 |
| 5,172,685 A * | 12/1992 | Nudelman | |
| 5,247,174 A | 9/1993 | Berman | 250/235 |
| 5,272,330 A | 12/1993 | Betzig et al. | 250/216 |
| 5,394,500 A | 2/1995 | Marchman | 385/123 |
| 5,425,123 A | 6/1995 | Hicks | 385/117 |
| 5,480,046 A | 1/1996 | Filas et al. | 216/7 |
| 5,570,441 A | 10/1996 | Filas et al. | 385/43 |
| 5,703,979 A | 12/1997 | Filas et al. | 385/43 |
| 5,715,337 A | 2/1998 | Spitzer et al. | 385/4 |
| 5,727,098 A | 3/1998 | Jacobson | 385/31 |
| 6,046,720 A | 4/2000 | Melville et al. | 345/108 |
| 6,091,067 A | 7/2000 | Drobot et al. | 250/234 |
| 6,161,035 A | 12/2000 | Furusawa | 600/476 |
| 6,211,904 B1 | 4/2001 | Adair et al. | 348/76 |
| 6,294,775 B1 | 9/2001 | Seibel et al. | 250/208.1 |
| 6,327,493 B1 | 12/2001 | Ozawa et al. | 600/476 |
| 2001/0055462 A1 * | 12/2001 | Seibel | 385/147 |
| 2002/0064341 A1 * | 5/2002 | Fauver et al. | 385/25 |

FOREIGN PATENT DOCUMENTS

| | | | | |
|---|---|---|---|---|
| EP | 1 142 529 A1 | 10/2001 | | A61B/1/00 |
| JP | 2001174744 A2 | 6/2001 | | G02B/26/10 |

* cited by examiner

Primary Examiner—Shawna J Shaw
(74) Attorney, Agent, or Firm—Ronald M. Anderson

(57) ABSTRACT

An integrated endoscopic image acquisition and therapeutic delivery system for use in minimally invasive medical procedures (MIMPs). The system uses directed and scanned optical illumination provided by a scanning optical fiber or light waveguide that is driven by a piezoelectric or other electromechanical actuator included at a distal end of an integrated imaging and diagnostic/therapeutic instrument. The directed illumination provides high resolution imaging, at a wide field of view (FOV), and in full color that matches or excels the images produced by conventional flexible endoscopes. When using scanned optical illumination, the size and number of the photon detectors do not limit the resolution and number of pixels of the resulting image. Additional features include enhancement of topographical features, stereoscopic viewing, and accurate measurement of feature sizes of a region of interest in a patient's body that facilitate providing diagnosis, monitoring, and/or therapy with the instrument.

87 Claims, 17 Drawing Sheets

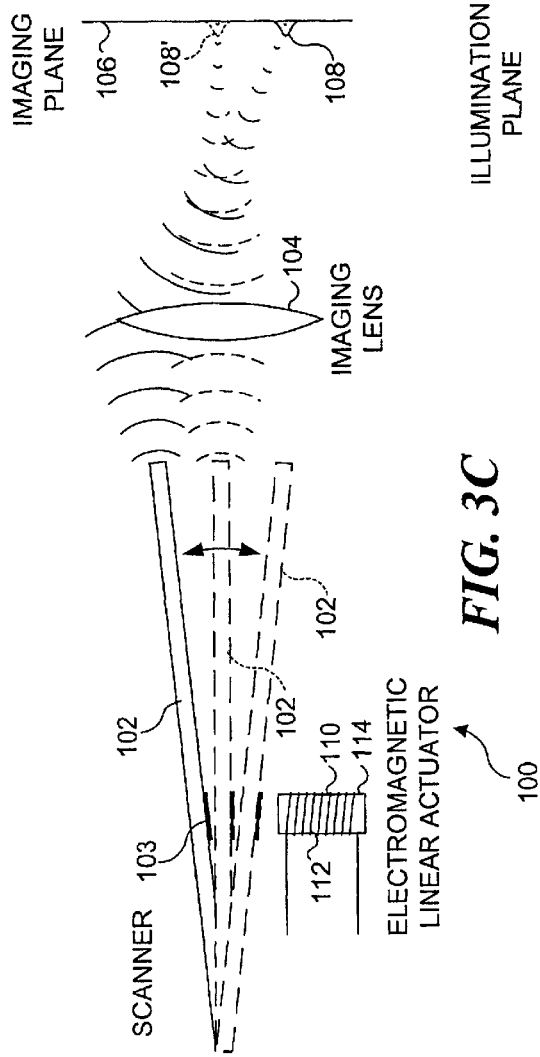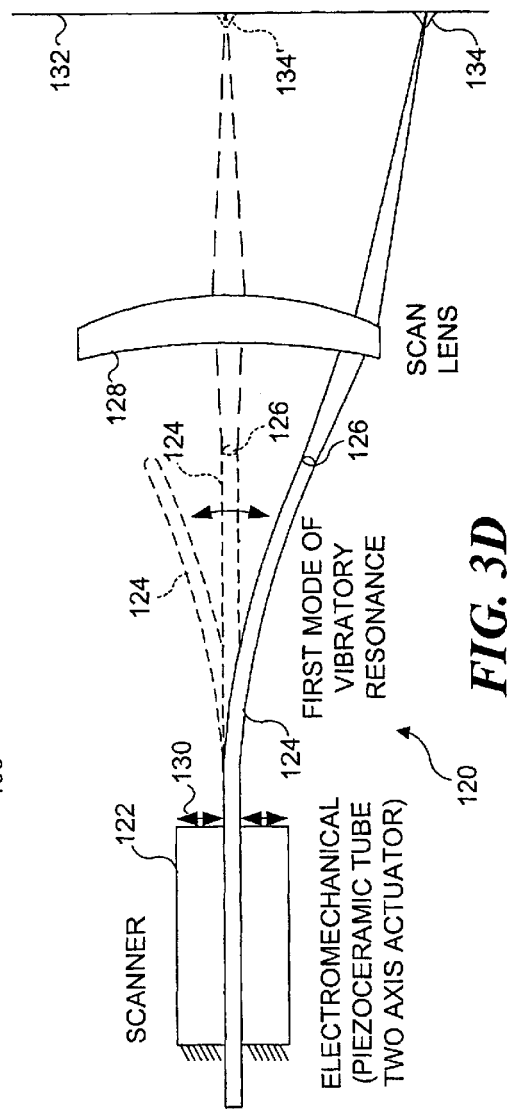

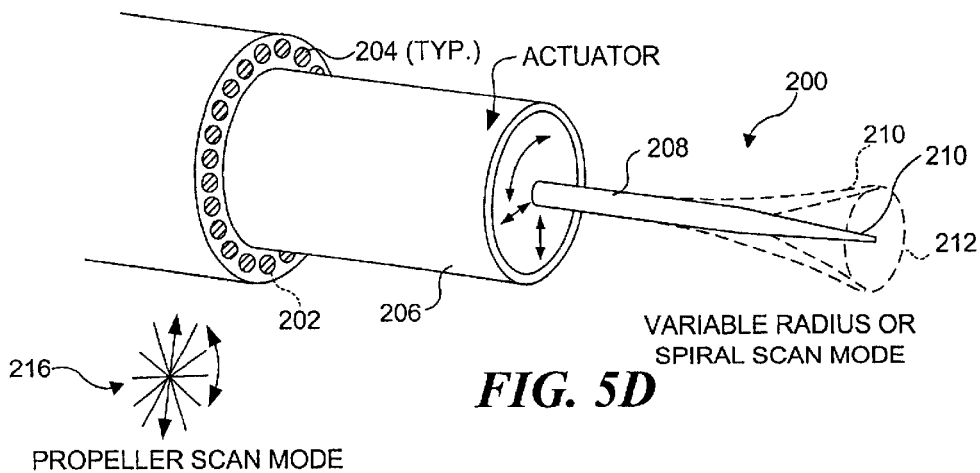
FIG. 5D
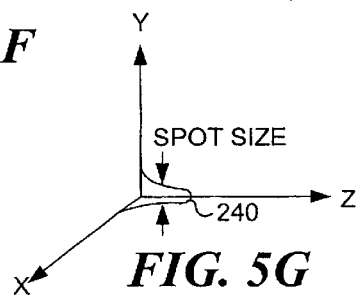
FIG. 5E
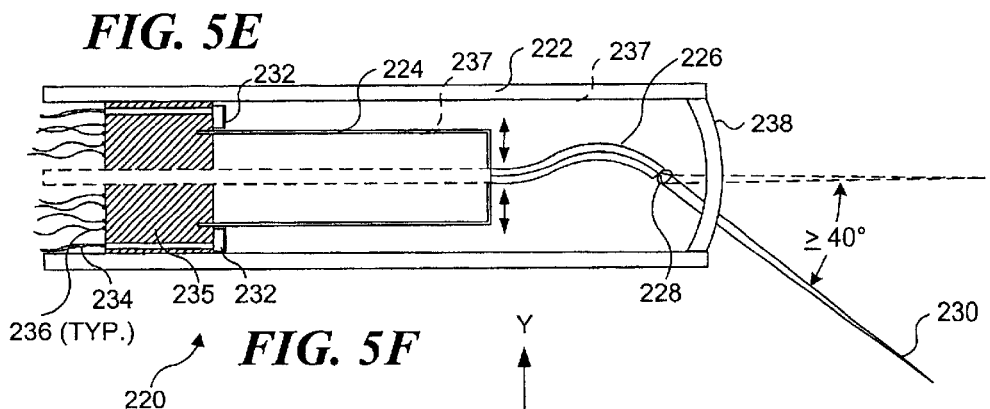
FIG. 5F
FIG. 5G
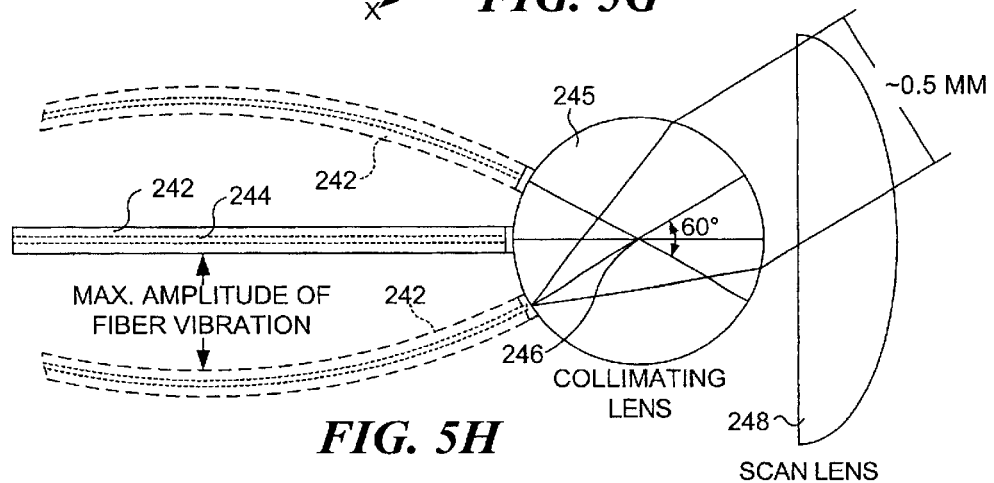
FIG. 5H

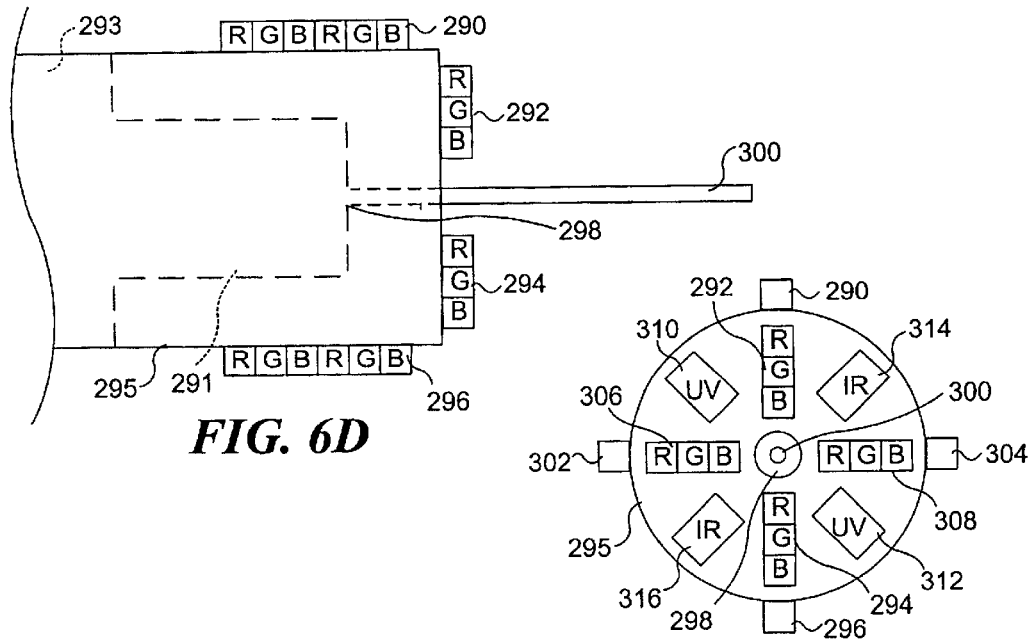
*FIG. 6D*
*FIG. 6E*
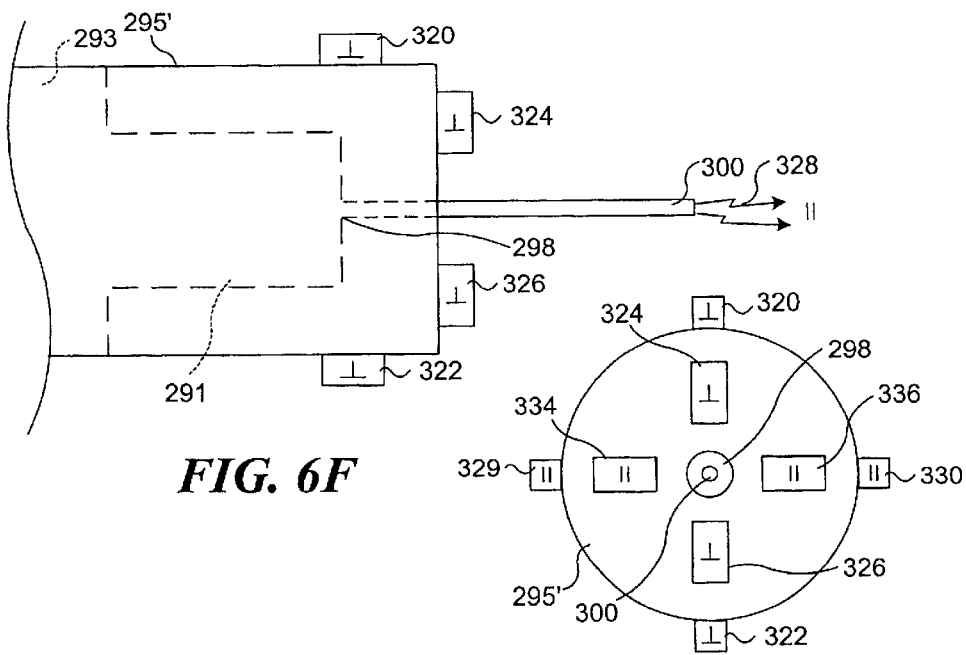
*FIG. 6F*
*FIG. 6G*

SINGLE SCANNING WAVEGUIDE USED FOR 3D IMAGING, DIAGNOSIS, & ASSISTING IN ENDOSCOPIC SURGERY

MEDICAL IMAGING, DIAGNOSIS, AND THERAPY USING A SCANNING SINGLE OPTICAL FIBER SYSTEM

RELATED APPLICATIONS

This application is based on prior copending provisional patent application Ser. No. 60/212,411, filed on Jun. 19, 2000, the benefit of the filing date of which is hereby claimed under 35 U.S.C. § 119(e).

FIELD OF THE INVENTION

The present invention generally relates to an optical fiber system that conveys light to and from a region of interest (ROI) on or within a living body, and more specifically, to a system that is selectively used for both imaging the ROI to facilitate a diagnosis, and for delivering therapy to the ROI.

BACKGROUND OF THE INVENTION

The burgeoning field of minimally invasive medical procedures (MIMPs) has increased the demand for systems that produce less tissue damage and trauma, faster recovery times, and lower risks to the patient. Ideally, the practitioner of MIMPs requires smaller instruments that perform a greater variety of functions. Furthermore, a "one-instrument-does-all" approach must add simplicity, not complexity, by ensuring that it is easy to use, minimizing the time required to master its operation.

The instruments used by practitioners of MIMPs typically include several different discrete systems for optical imaging, monitoring, maneuvering, sizing, diagnosis, biopsy, therapy, surgery, and non-visual monitoring/sensing. It would be preferable to combine the functions provided by these instruments in a single compact device to reduce the number of surgical ports that are currently required for a plurality of single-function tools. By employing an integrated multi-functional tool so that only one small port is used, the risks associated with repeatedly removing and inserting surgical tools can be dramatically reduced. Since most MIMPs require the practitioner to constantly monitor the procedure visually, optical imaging is considered a requirement for any fully integrated system for MIMPs. Thus, an appropriate multifunction instrument will most likely include an optical imaging system, and the imaging system should be integrated with one or more diagnostic, and/or therapeutic tools.

The current tools used for MIMPs cannot readily be integrated without increasing the size of the resultant instrument to an excessive degree. All commercial optical imaging systems that include a maneuverable flexible shaft must maintain a certain size (diameter) in order to preserve image quality. Currently, flexible scopes cannot be made smaller than this limit unless image field of view (FOV) or resolution is sacrificed. Although imaging and some diagnostic capability can be integrated into existing scopes, such as standard tissue imaging in combination with fluorescence for early detection of cancers, the optical systems of current flexible scopes cannot provide integrated diagnoses and therapies at the required degrees of performance, size, and price that will be demanded in the future by medical practitioners.

Current Technology Used for MIMPs

Presently available flexible scope designs use either a bundle of optical fibers (optical waveguides) and/or one or more cameras having an array of detectors to capture an image. Thus, the diameter of these flexible scopes employed for remote imaging cannot be reduced to smaller than the image size. Ignoring the optical fibers used for illumination, the scope diameter is therefore limited by the individual pixel size of a camera or by the diameter of optical fibers used to acquire the image. Currently, the smallest pixel element is determined by the size of the end of an optical fiber, which has a minimum core diameter of about 4 $\mu$m. To propagate light through an optical fiber, a surrounding cladding layer is required, increasing the minimum pixel size to more than 5 $\mu$m in diameter. If a standard VGA image is desired (e.g., with a resolution of 640×480 pixels), then a minimum diameter required for just the image optical fiber is more than 3 mm. Therefore, resolution and/or FOV must be sacrificed by having fewer pixel elements in order to achieve scopes with less than 3 mm overall diameter. All commercially available scopes suffer from this fundamental tradeoff between high image quality and small size.

Thus, it would be desirable to add diagnostic and therapeutic or surgical capability to a remote imaging system for the purpose of reducing the overall size of the instrument used for MIMPs. Since, for the reasons noted above, the current design for flexible scopes cannot readily be reduced in size without reducing imaging performance, the options for integrating diagnostic and therapeutic applications with an imaging system would appear to require an increase in the size of the instrument or use of separate instruments for each function. For example, a high intensity light source might be added to a general endoscopic surgical system to carry out photodynamic therapy (PDT) or laser surgery, or a polarized light source or other special light source might be needed for diagnosis and/or sensing a condition of an ROI. However, the white light illumination for standard endoscopic imaging is typically provided through an optical fiber bundle that diffusely illuminates the tissue and is incapable of providing a directed optical energy at high intensity and resolution to produce effective optical therapies, and will often not have the characteristics required for diagnostic processes. Therefore, any optical therapies that require directed illumination of high intensity light, such as PDT and laser surgery, or any diagnostic processes that also require a special light source cannot use existing optical designs for flexible imaging scopes, but instead, must rely on a second optical pathway and separate control mechanisms.

To perform diagnostic or therapeutic MIMPs, one or more separate instruments are used within the FOV of a standard endoscopic imager, and any additional separate instrument often must be held and maneuvered by a second medical practitioner. Typically, the second instrument provides a high intensity point source of light for optical therapies, a hot-tipped probe for thermal therapies, or a trocar used for mechanical cutting. The second instrument is moved to the surface of the tissue and usually moved within or across the surface of the tissue, covering the area of interest as the tool is scanned and manipulated by hand. These secondary instruments are inserted into the patient's body through a separate port, and thus, while being used, are viewed from a different point of view in the visual image. Furthermore, the therapeutic instrument often blocks the practitioner's direct view of the ROI with the imaging tool, making highly accurate therapies quite difficult for the medical practitioner to achieve. Significant amounts of training and practice are required to overcome these difficulties, as well as the capability to work with a reduced sense of touch that is conveyed through the shaft of an instrument having friction and a non-intuitive pivot at the point of entry. Thus, to work effectively with current imaging and therapeutic technologies, the practitioner of MIMPs must be highly trained and skilled.

Clearly, there is a need for an instrument that integrates imaging, diagnostic, and therapeutic functions, delivers these functions through a relatively small diameter, and is sufficiently intuitive to use as to require little training or skill. Ideally, the instrument should be implemented using a single optical fiber, but should still be capable of providing a sufficient FOV, good image size, and resolution, and should ensure that the ROI within a patient's body while administering therapy corresponds to that during imaging. Currently, none of the instruments available provide these capabilities and cannot be easily modified to provide such capabilities.

SUMMARY OF THE INVENTION

In accord with the present invention, apparatus is defined for selectively providing imaging, monitoring, sensing, screening, diagnosis, and therapy for an ROI in a patient. The apparatus preferably includes at least one light source. For example, a light source may be used to provide both an illumination light for imaging light, while another light source produces light of a substantially different characteristic than the imaging light for other uses. Or, the same light source can be used for both imaging and the other purpose. Also included is a light guide having a proximal end and a distal end. (Note that in the claims that follow, the term "light guide" or its plural form is used, and these terms will be understood to encompass optical fibers, thin film optical paths, and other devices and constructs for conveying light along a desired path.) The one or more light sources are optically coupled to the proximal end of the light guide, and the distal end of the light guide is adapted to be positioned adjacent to an ROI. A scanning actuator is disposed adjacent to the distal end of the light guide and causes the light from the one or more light sources that are conveyed through the light guide to scan the ROI. A light detector receives light from the ROI, producing a signal corresponding to an intensity of the light for use in producing an image of the ROI. Also included are a display on which the image of the ROI can be visualized by a user, and a control circuit that is operatively coupled to control the scanning actuator, the one or more light sources, and the light guide. The control circuit selectively energizes the one or more light sources to image the ROI and render at least one other function to the ROI. The other functions include diagnosing a condition, rendering therapy, sensing a condition, and monitoring a medical procedure—all in regard to the ROI.

In one embodiment of the present invention, a plurality of light sources emit light of different colors. The apparatus then further includes a combiner that combines the light of different colors emitted by the plurality of light sources for input to the proximal end of the light guide. Also, for this embodiment, the light detector includes a plurality of light sensors that are each sensitive to one of the different colors of light emitted by the plurality of light sources. In one form of this embodiment, the plurality of light sensors are disposed adjacent to the distal end of the light guide, while in another form of the embodiment, a plurality of light guides convey the imaging light reflected from the ROI to the plurality of light sensors. A quasi-stereo image of the ROI can be visualized by a user, by employing different portions of the plurality of light guides to convey the light reflected from spaced-apart areas in the ROI. A stereo display is then preferably included to enable a user to visualize the quasi-stereo image of the ROI.

One form of the scanning actuator includes a pair of electromechanical actuators that respectively move the distal end of the light guide in substantially transverse directions. In another embodiment, the scanning actuator comprises a piezoceramic actuator that is energized at a harmonic of a resonant frequency of the distal end of the light guide or electromechanical actuator.

In one configuration, the light guide comprises an optical fiber, and the distal end of the optical fiber is tapered to a substantially smaller cross-sectional size than a more proximal portion of the optical fiber, producing a tapered end that emits light having a substantially smaller point spread function (PSF) than light that would be emitted from a non-tapered end of an optical fiber.

In most embodiments of the present invention, at least one lens is disposed between the distal end of the light guide and the ROI, for focusing the imaging light and the light produced by the therapy light source onto the ROI. Preferably, to provide high resolution and a good FOV, a lens is mounted on the distal end of the light guide in one embodiment. In this configuration, as the scanning actuator drives the distal end of the light guide in a resonance mode to scan the ROI, the lens that is mounted on the distal end of the light guide has sufficient mass so that the lens generally rotates about a center of the lens as the light guide moves. The movement of the light guide changes the direction in which light is emitted from the lens, to scan the ROI.

In yet another embodiment, the light guide comprises a thin film optical waveguide that is optically coupled to the distal end of the light guide so that light emitted by the at least one light source is directed onto the ROI. The scanning actuator is then disposed adjacent to the thin film optical waveguide and moves the thin film optical waveguide, to cause the light to scan the ROI. Preferably, the thin film optical waveguide has a cross-sectional size less than 0.01 mm. It is also contemplated that a plurality of thin film optical waveguides can be used in parallel to convey light to and from the ROI.

In one embodiment, a polarizing filter is disposed between the at least one light source and the ROI, so that the ROI is illuminated with a polarized illumination light. For this embodiment, the light detector detects polarized light having a predefined axis of polarization.

In still another embodiment, the at least one light source provides one or more of a visible light, an ultraviolet (UV) light, and an infrared (IR) light as the illumination light. In connection with this embodiment, the light detector is responsive to a corresponding one or more of the visible light, UV light, and/or IR light. In regard to another alternative embodiment, the light detector is responsive to light emitted from the ROI due to either a phosphorescence or a fluorescence.

Either a spectrophotometer or a spectrum analyzer are preferably coupled to the light detector for use in determining a condition of the ROI. Optionally, a thermal detector (which may be an optical type of detector) is coupled to one of the proximal and distal ends of the light guide for use in monitoring a temperature in the ROI.

The apparatus also preferably includes means adapted for guiding and maneuvering the distal end of the light guide to the ROI within a patient. In some cases where it is necessary to stabilize the distal end of the light guide, a balloon disposed adjacent to the distal end of the light guide is inflated in a cavity or passage within a patient's body.

BRIEF DESCRIPTION OF THE DRAWINGS FIGURES

The foregoing aspects and many of the attendant advantages of this invention will become more readily appreciated as the same becomes better understood by reference to the following detailed description, when taken in conjunction with the accompanying drawings, wherein:

FIGS. 3C and 3D illustrate two alternative embodiments for actuators for driving the scanning optical fiber of FIGS. 3A and 3B, with an imaging lens and a scan lens, respectively;

Figure 3A:
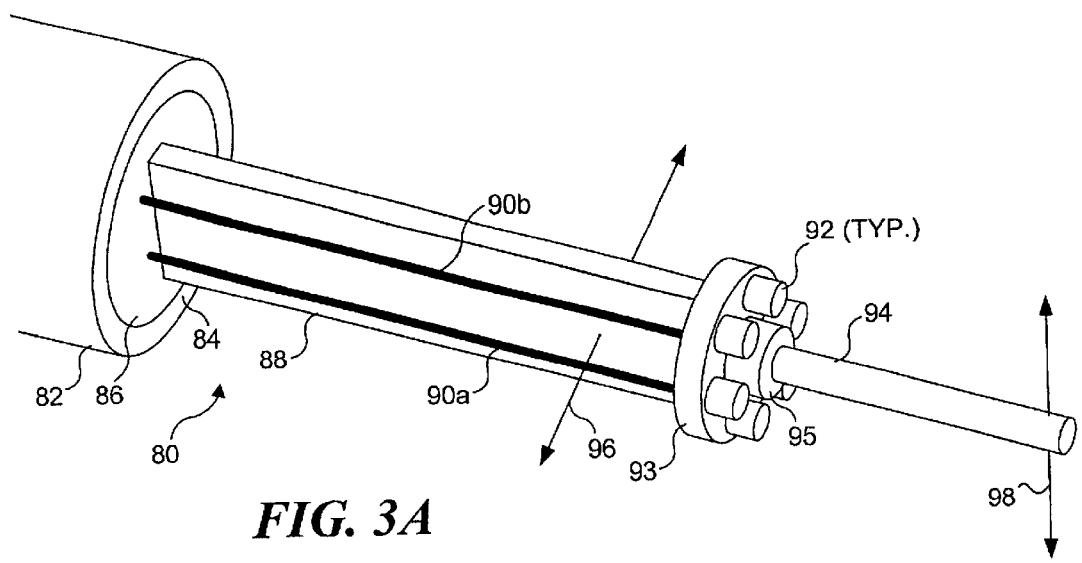
FIGS. 3A and 3B illustrate components of a rectilinear scanning optical fiber capable of selectively scanning in either or both of two transverse directions.
Figure 3B:
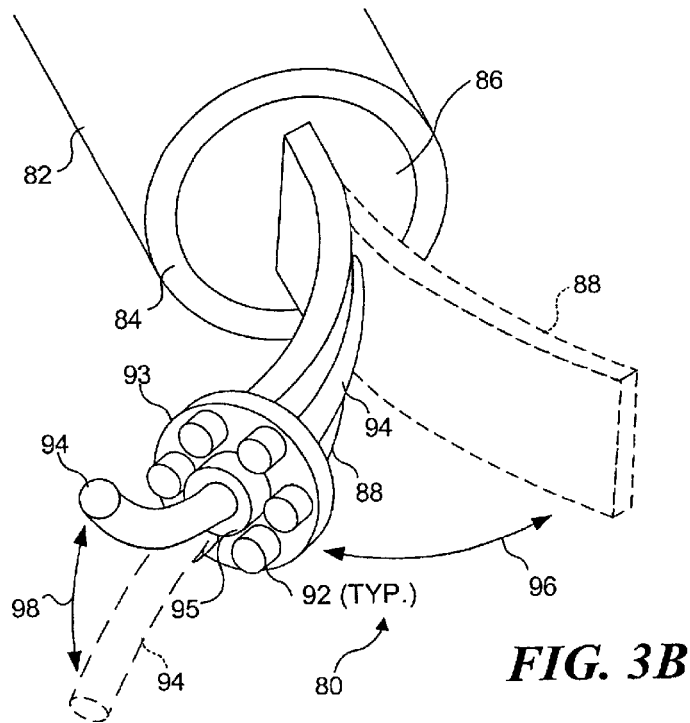
Figure 4A:
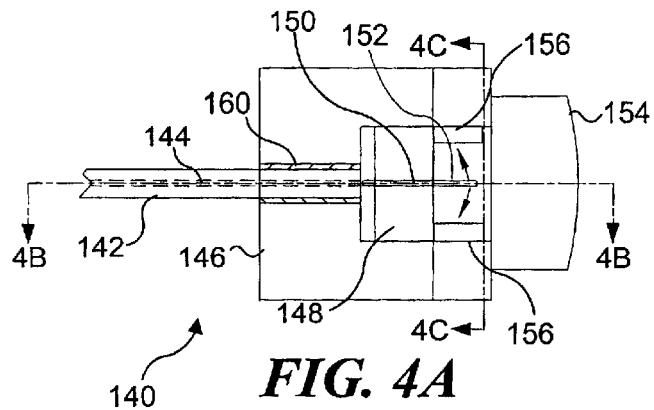
Figure 4B:
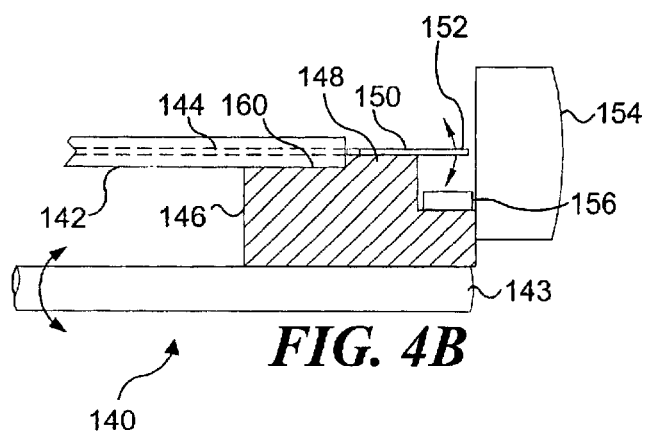
Figure 4C:
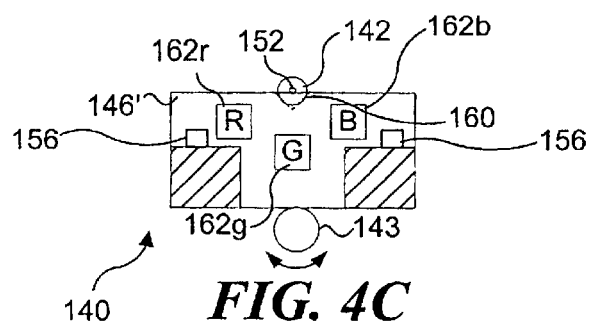
Figure 4D:
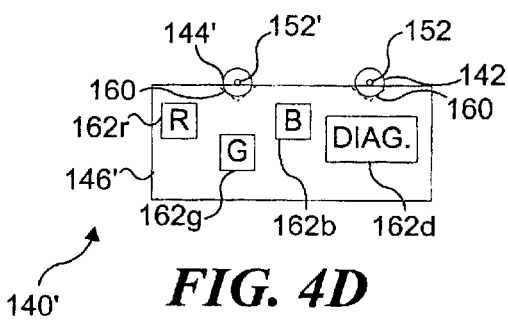
Figure 5A:
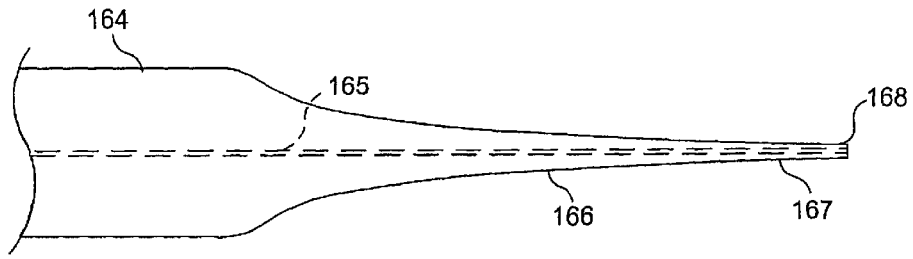
Figure 5B:
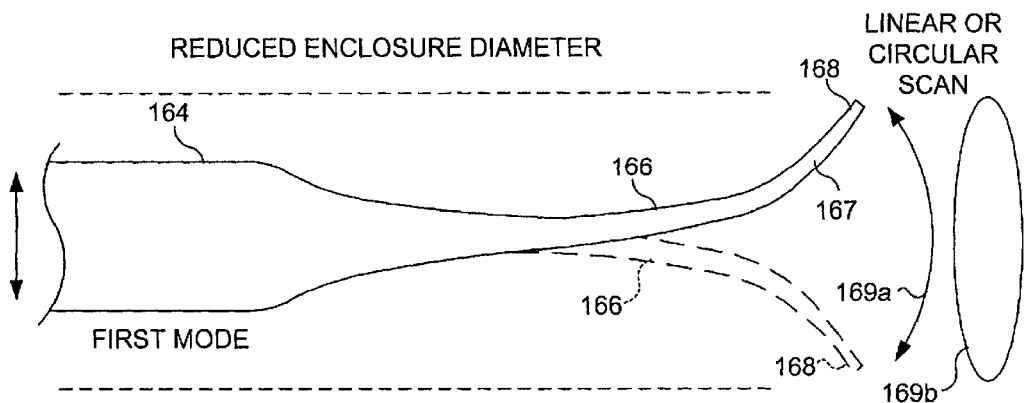
Figure 5C:
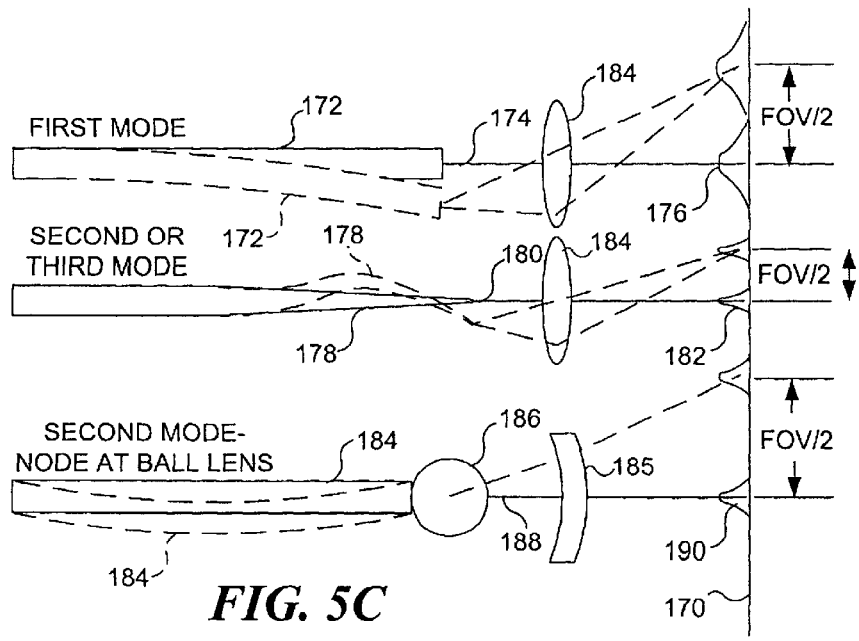
Figure 6A:
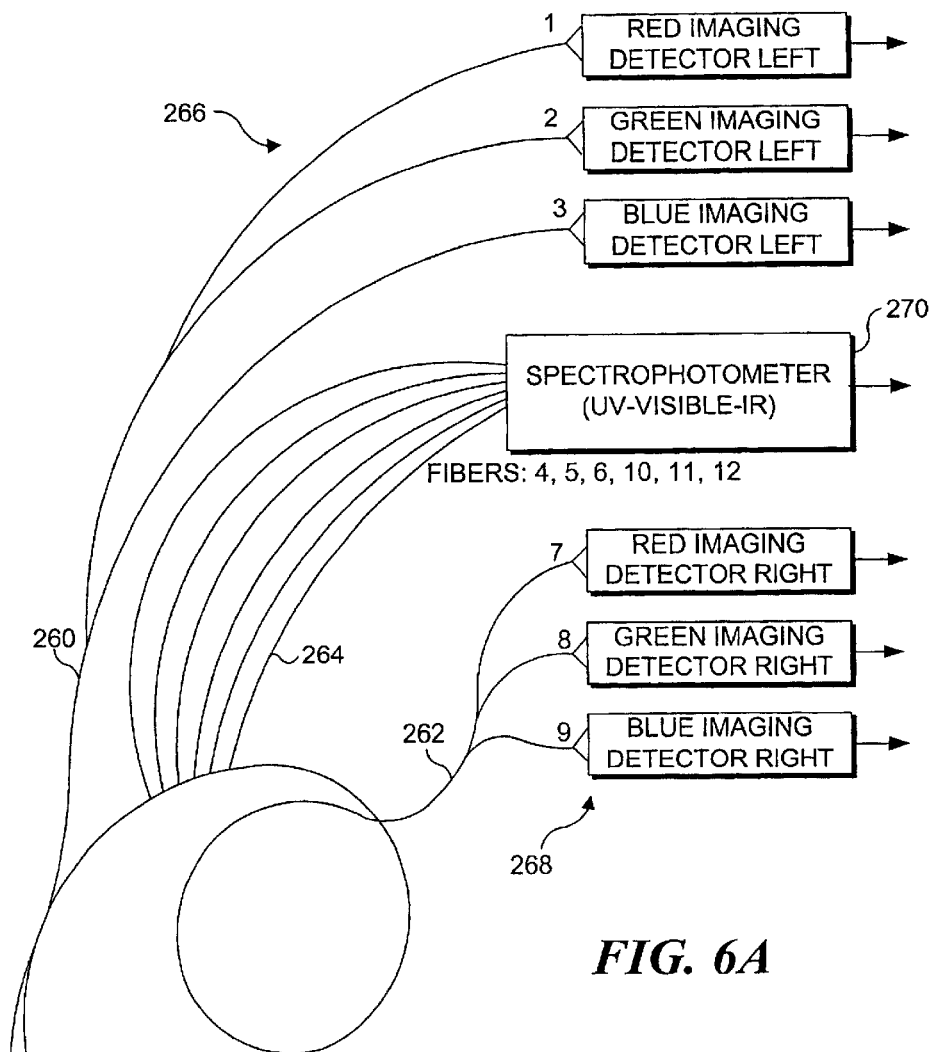
Figure 6A:
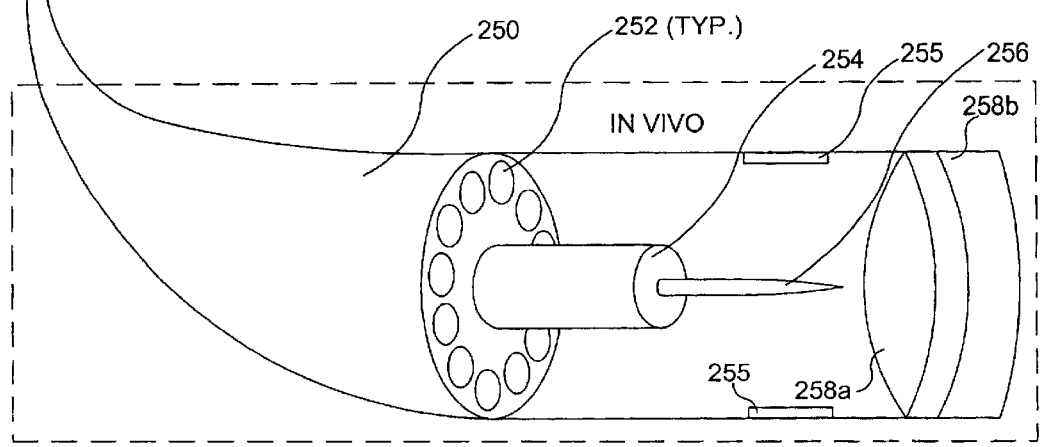
Figure 6B:
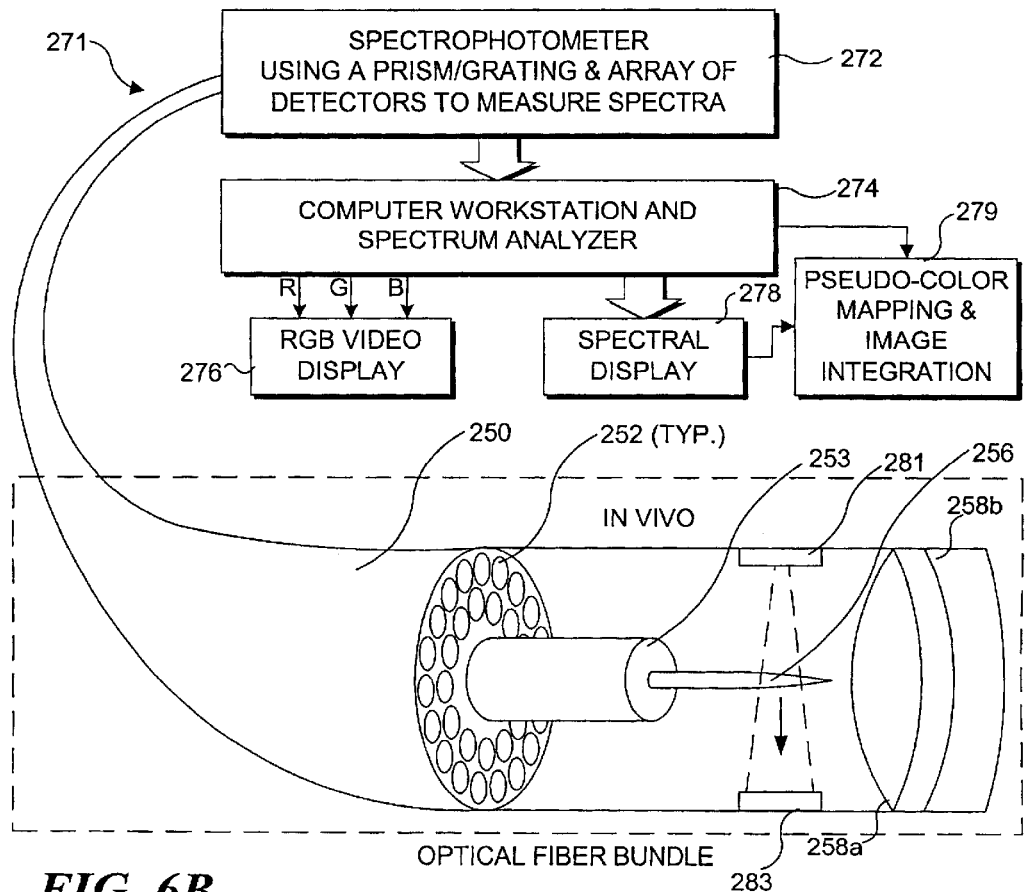
Figure 6C:
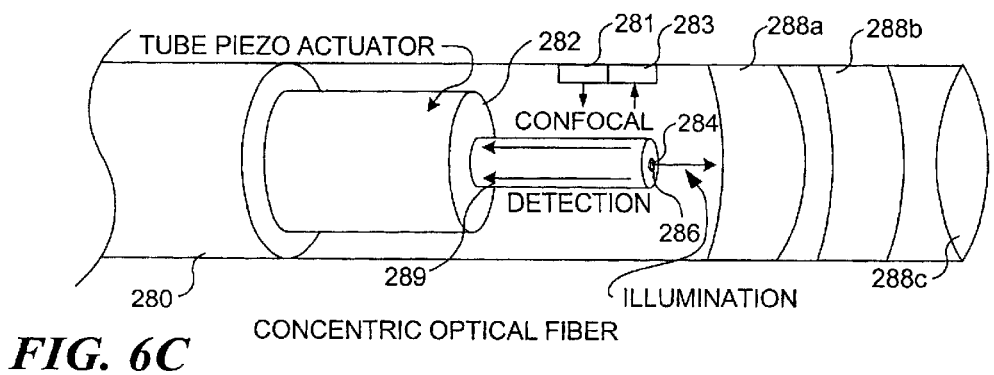
Figure 7A:
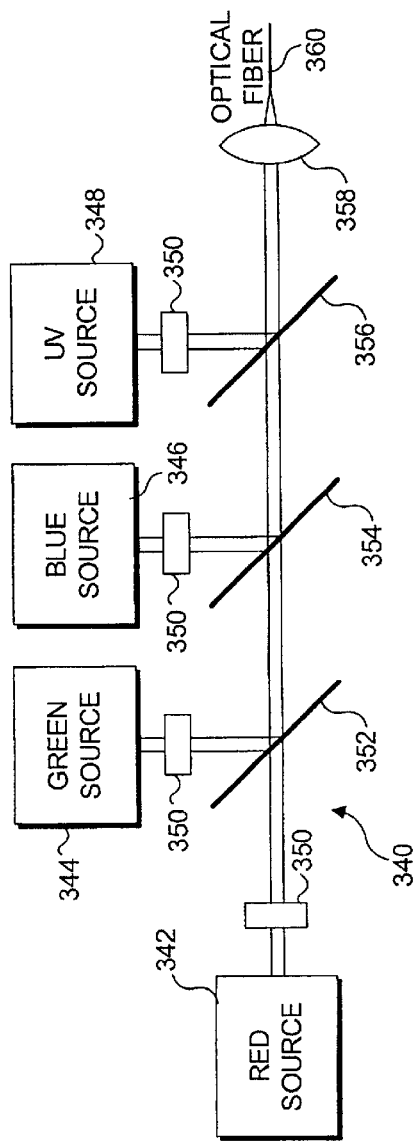
Figure 7B:
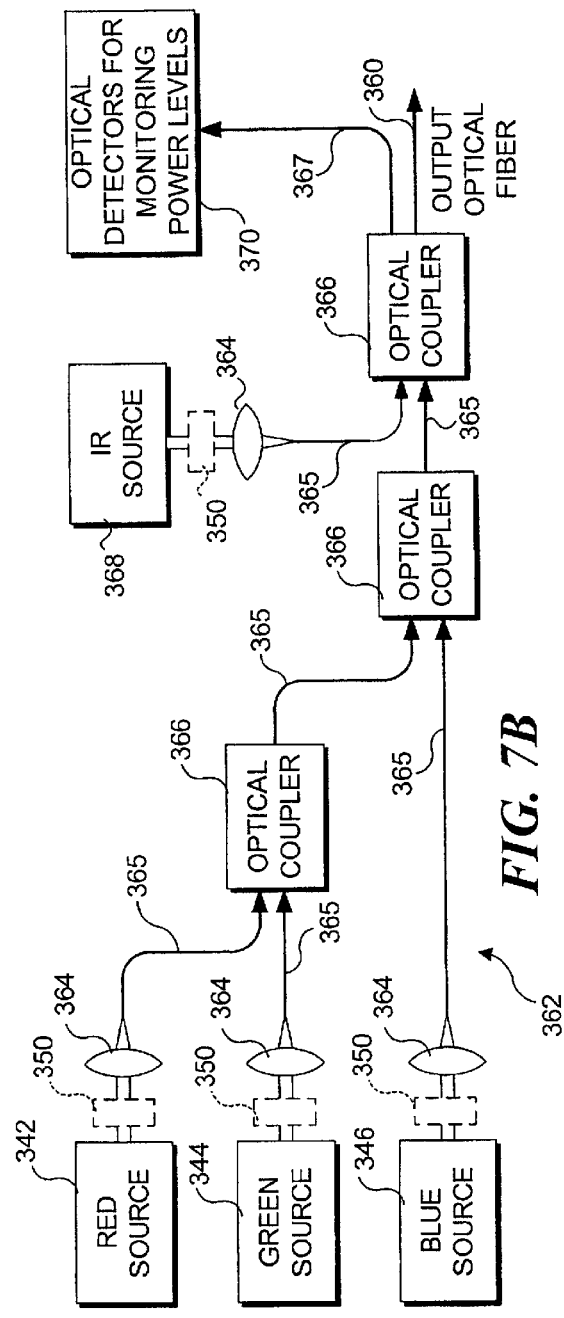
Figure 7C:
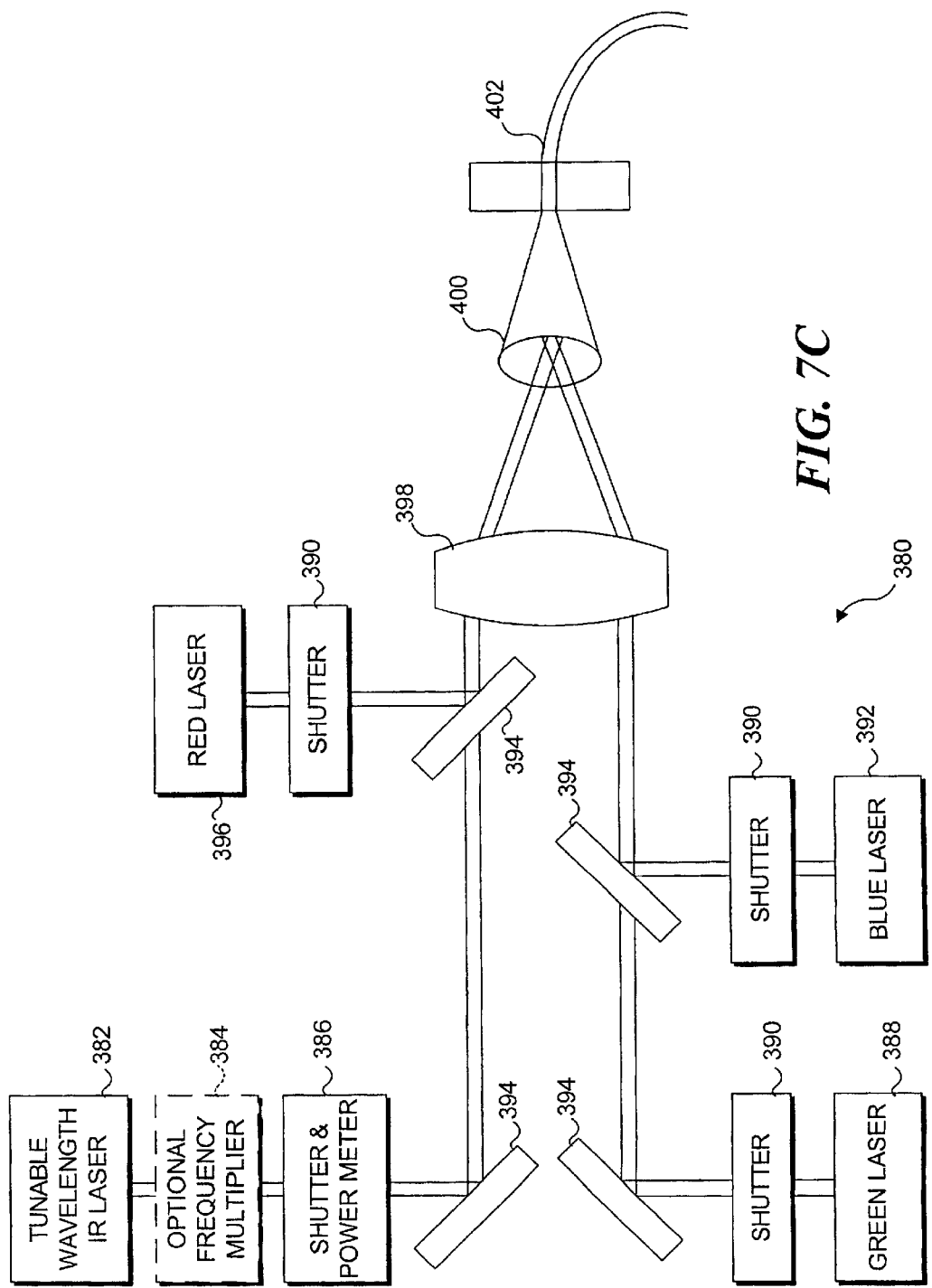
Figure 8:
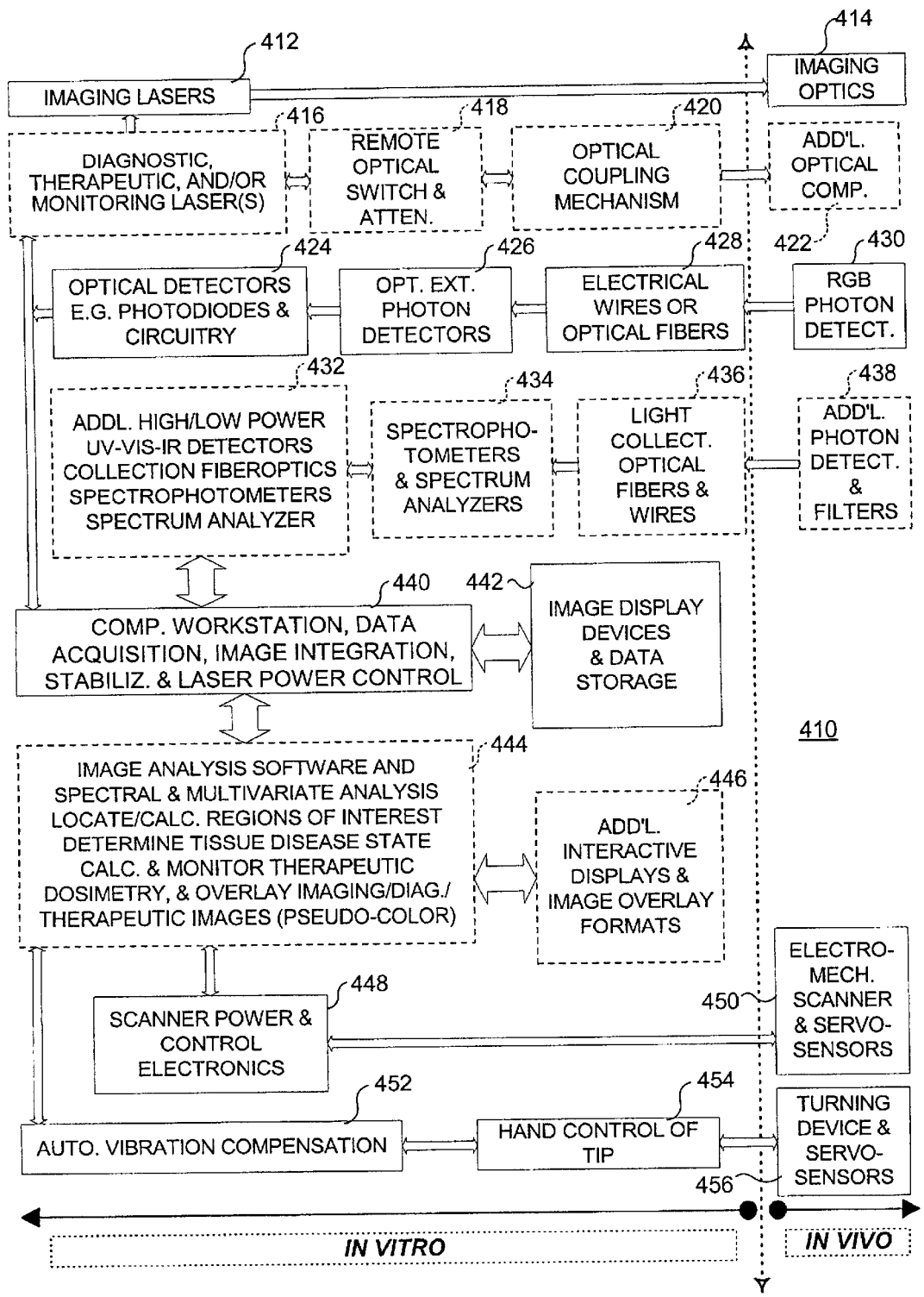
Figure 9A:
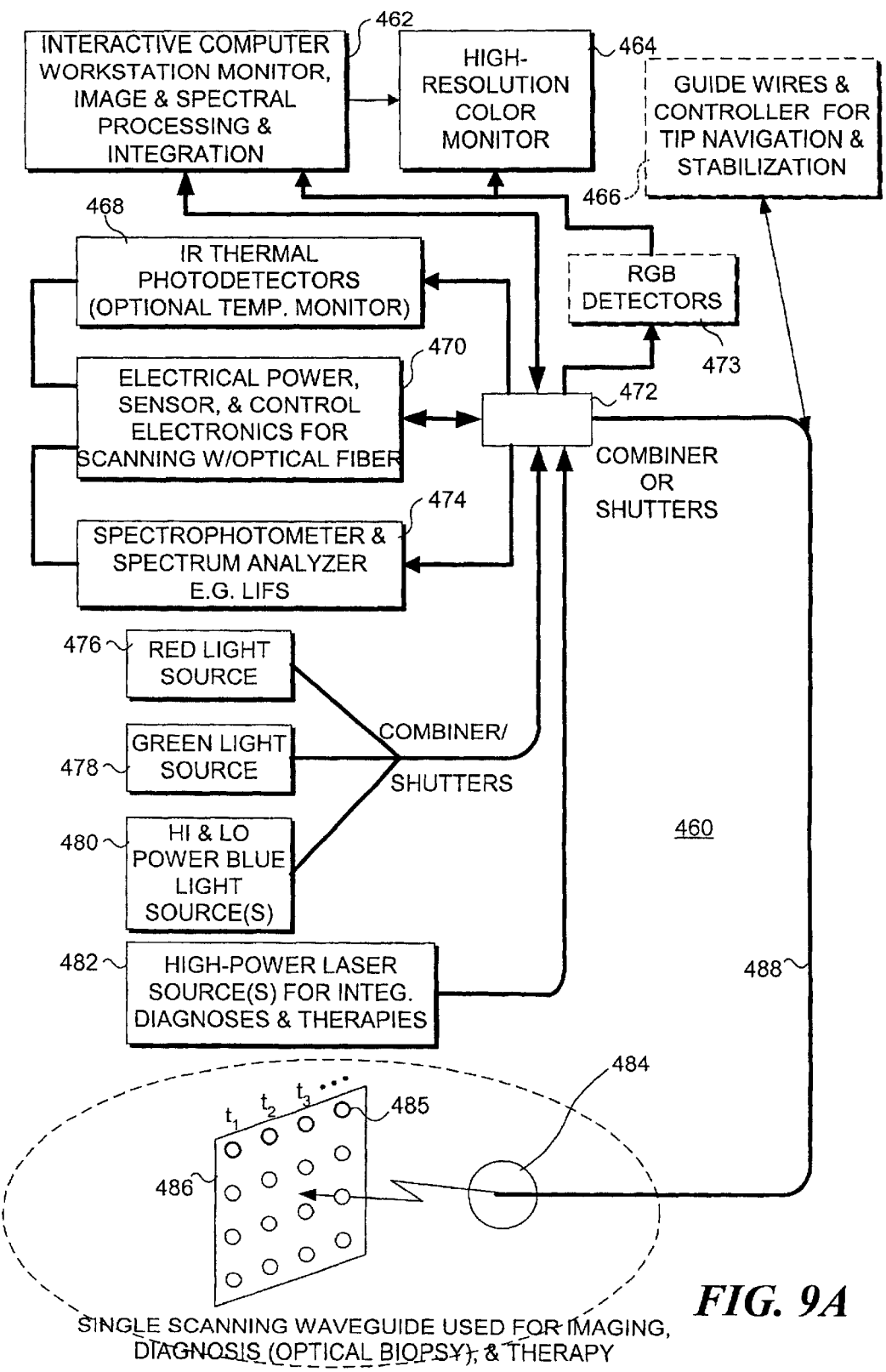
Figure 9B:
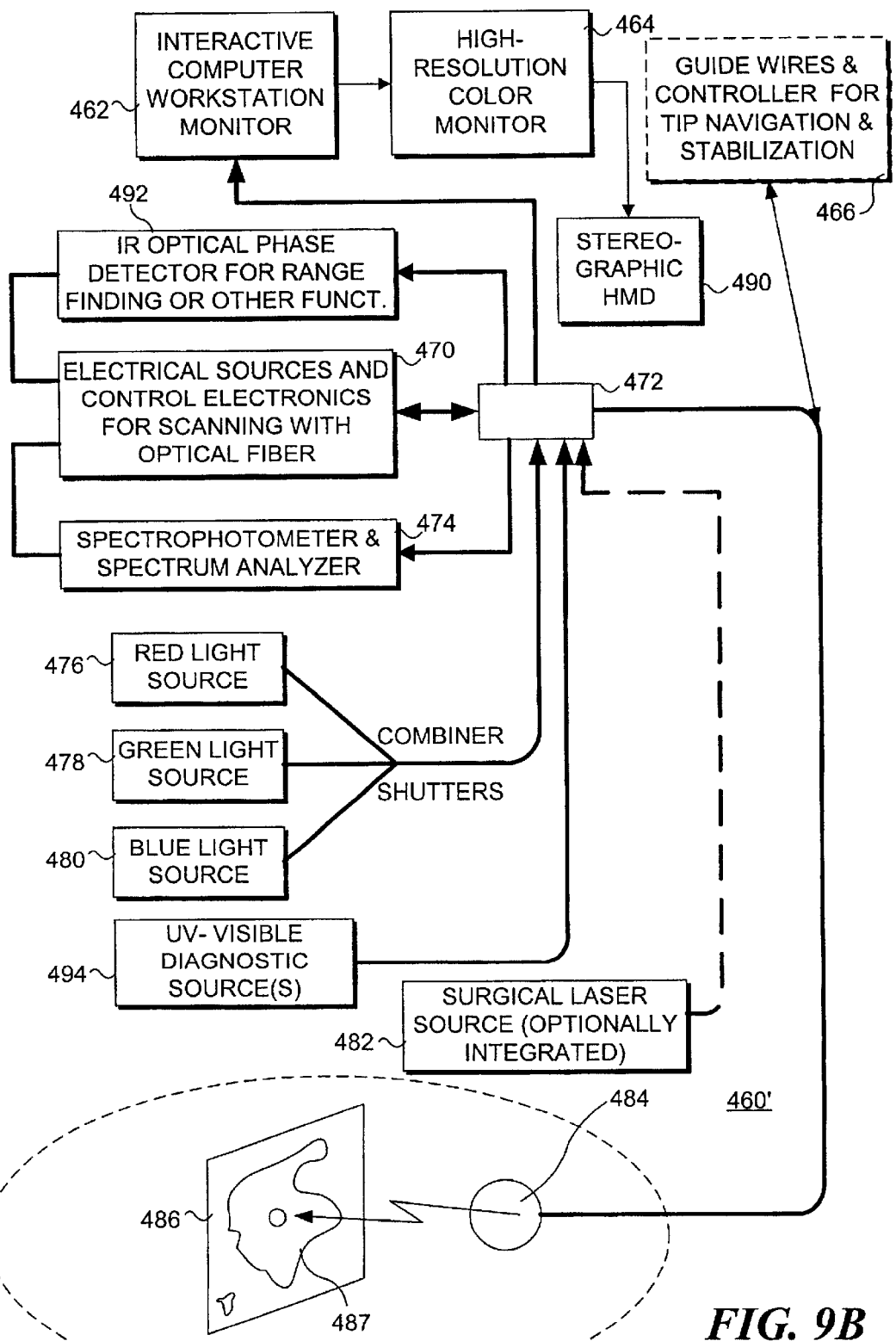
Figure 10:
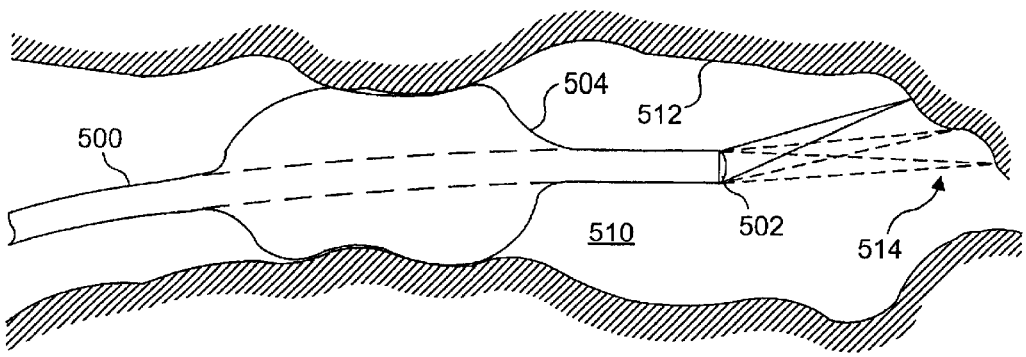
Figure 11A:
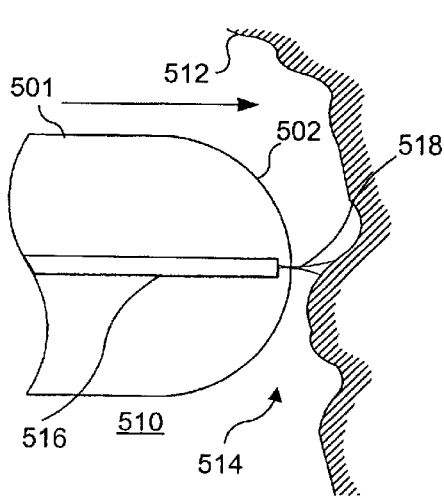
Figure 11B:
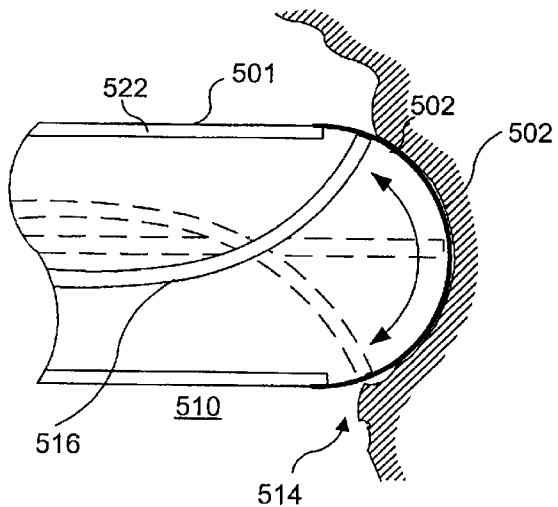
Figure 11C:
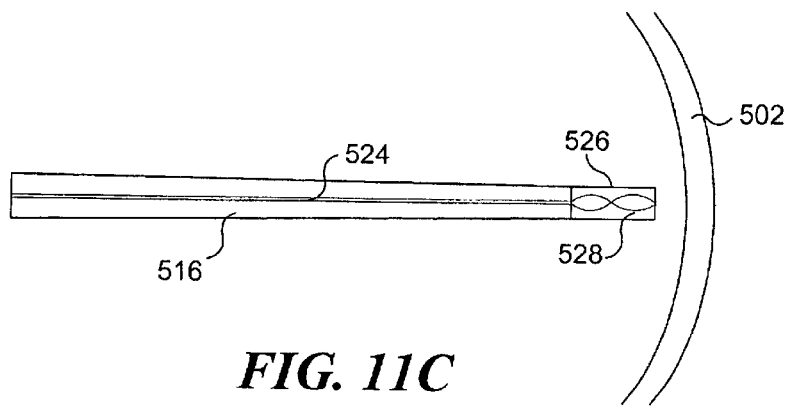
Figure 12:
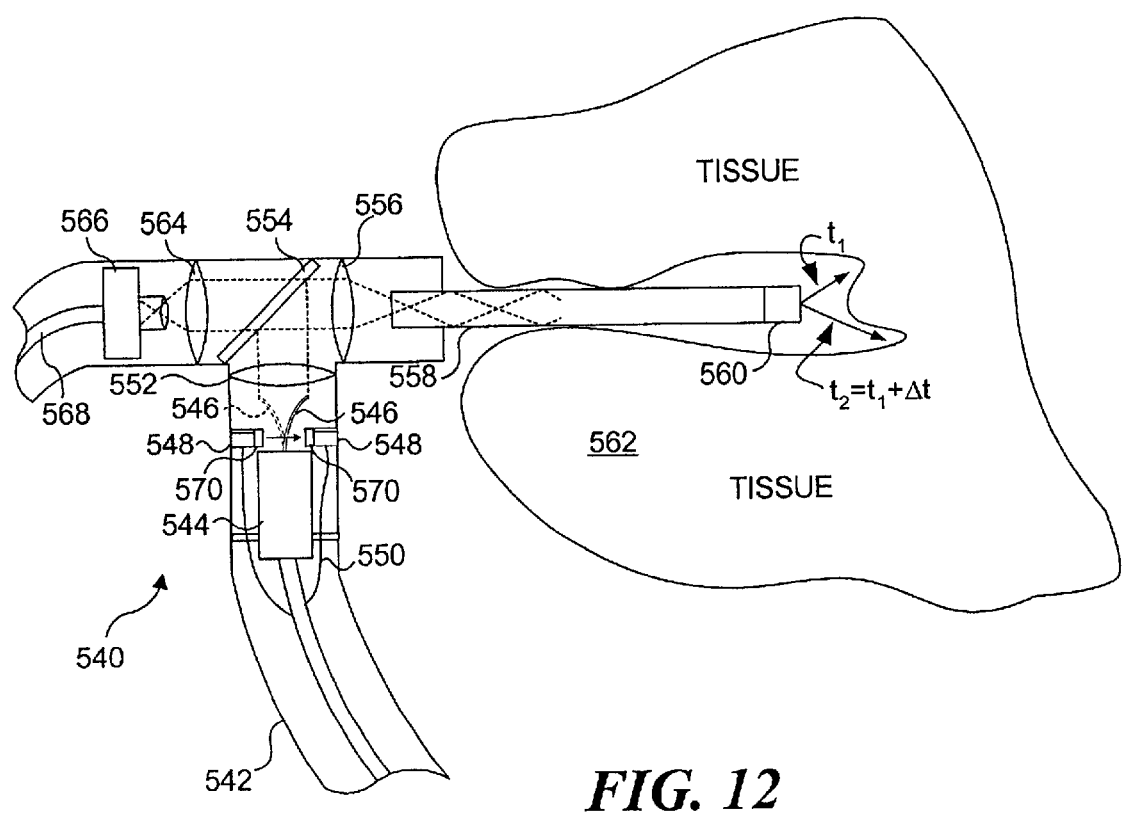

FIGS. 4A, 4B, and 4C respectively illustrate a top plan view, a side elevational cross-sectional view taken along section line 4B—4B in FIG. 4A, and an end view taken along section line 4C—4C in FIG. 4A, of a first embodiment of a thin film, rectilinear illuminator that is similar in scanning function to the embodiment of FIGS. 3A and 3B;

FIG. 4D illustrates an end elevational view of a second embodiment that includes a pair of thin film parallel cantilevers for illumination of an ROI;

FIGS. 5A and 5B illustrate a distal end of a conventional optical fiber that has been micro-fabricated to form a taper, and the extreme linear or oval deflection of the distal end at resonance is shown in FIG. 5B;

FIG. 5C illustrates the relative PSF for three different tip profiles of a scanning optical fiber;

FIG. 5D illustrates the variable radius circular, or spiral scanning mode of a tapered optical fiber in accord with the present invention;

FIG. 5E illustrates a propeller scan mode motion in which an optical fiber can be driven;

FIG. 5F is a schematic diagram of an optical fiber probe fitted with a ball lens and moving in a second mode of mechanical resonance;

FIG. 5G illustrates the three-dimensional (3D) PSF for the optical fiber configuration of FIG. 5F;

FIG. 5H is a schematic illustration of an optical fiber on which a ball lens used for collimating light has been mounted;

FIG. 6A is a schematic diagram showing the configuration of distal optical fiber position sensors and proximally disposed photon detectors with proximal optical fiber light collectors that are capable of quasi-stereo image acquisition;

FIGS. 6B and 6C are schematic diagrams respectively showing an alternative configuration for proximal photon filtration and detection using a bundle of optical fibers and a single concentric core optical fiber, the latter being incapable of quasi-stereo image acquisition;

FIGS. 6D and 6E schematically illustrate distal photon red, green, blue (RGB) filtration and detection using stereo-paired geometry and the ability to subtract background scatter using forward and side-facing spatial arrangements of detectors, respectively shown in a side elevational view and in an end view;

FIGS. 6F and 6G schematically illustrate distal photon polarized filtration and detection using stereo-paired geometry and the ability to enhance signals from superficial tissue using forward and side-facing spatial arrangements of detectors, respectively shown in a side elevational view and in an end view;

FIG. 7A is a schematic diagram of an optical fiber system that employs radiation from visible and UV laser sources combined with dichroic filters;

FIG. 7B is a schematic diagram of an optical fiber system that employs radiation from visible and IR laser sources combined with fiber optic combiners connected in series;

FIG. 7C is a schematic diagram of an optical fiber system that includes a tunable wavelength laser source and standard RGB imaging light sources combined with a tapered hollow tube;

FIG. 8 is a block diagram illustrating the functional input and output components of an optical fiber system in accord with the present invention;

FIG. 9A is a functional block diagram of an integrated cancer imaging, screening, and biopsy system, with optical therapy delivery and monitoring capabilities in accord with the present invention;

FIG. 9B is a functional block diagram of an integrated tumor imaging and diagnostic system, with stereograph surgical support and display capabilities in accord with the present invention;

FIG. 10 is a side elevational view of the distal end of an optical fiber having an inflatable balloon for anchoring the optical fiber in place adjacent to a treatment site;

FIGS. 11A, 11B, and 11C illustrate an embodiment of an optical fiber that does not include any imaging lens between the distal end of the optical fiber and an ROI; and FIG. 12 is a cross-sectional view of an embodiment of the present invention that is incorporated into a rigid endoscope.

DESCRIPTION OF THE PREFERRED EMBODIMENTS

Prior Art Imaging Endoscopes

Figure 1A:
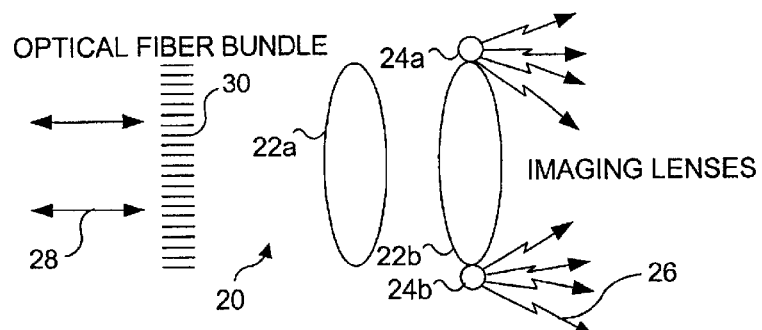
FIG. 1A (Prior Art) is a schematic view of the distal end of a non-scanning flexible endoscope in which each detector is a single image pixel.

With reference to FIG. 1A, the distal end of a flexible endoscope 20 is illustrated schematically, indicating how a non-scanning imaging process is implemented. Imaging lenses 22a and 22b receive light reflected from an ROI within a patient's body illuminated with light sources 24a and 24b. Although shown adjacent imaging lens 22b, these light sources may alternatively be disposed external to the patient's body so that light produced by the sources is conveyed through optical fibers (not shown) to the internal site. Light that has passed through imaging lenses 22a and 22b is received by a pixel array optical fiber bundle 30 (or alternatively by a pixel array camera—not shown). In this case, each camera or detector disposed at the distal end within a patient's body, or proximally at the end of the fiber optic bundle through which the light from imaging lenses 22a and 22b is conveyed outside the patient's body, corresponds to only a single image pixel. As noted above, the size of the optical fibers or of the array required for producing an overall image of the diffusely illuminated ROI is limited by the diameter of endoscope 20.

Figure 1B:
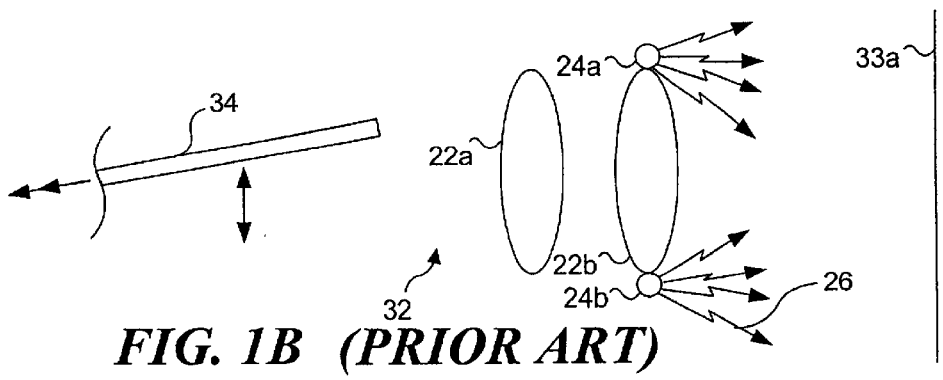
FIG. 1B (Prior Art) is a schematic view of a cantilevered scanning optical fiber that detects each pixel in a time series sequence.

A time series pixel endoscope 32, which is shown in FIG. 1B, detects each successive pixel at an image plane 33a. As before, imaging lenses 22a and 22b focus the image on image plane 33a, which is then scanned by a cantilevered optical fiber 34 so that light corresponding to each successive pixel in an image is transmitted through the cantilevered optical fiber and added to the previously transmitted image pixel data to be displayed at the proximal end of the time series pixel endoscope. Since only one or perhaps a few optical fibers are required to convey the stream of pixel light data to the proximal end of the time series pixel endoscope, the shaft of the endoscope can be made much smaller in diameter than the non-scanning design shown in FIG. 1A. Cantilevered optical fiber 32 is preferably a multi-mode type fiber, and receives the diffuse illumination provided by light sources 24a and 24b reflected from the ROI within the patient's body. It should be noted that this prior art scanning device is only used for imaging an ROI that is diffusely illuminated, as is true of virtually all conventional endoscopic illumination systems.

Scanning Devices Used in the Present Invention

In contrast to the prior art devices illustrated in FIGS. 1A and 1B, the present invention integrates both imaging and non-imaging functionality, such as diagnosis, monitoring, and therapy of an internal ROI, instead of requiring separate instruments for imaging and for rendering therapy or other functions to a site. Many optical diagnostic and therapeutic techniques rely on high quality illumination at elevated intensities, which is inherent in optical scanning and cannot be achieved with diffuse illumination. A scanned beam of intense optical energy is more effective at overcoming the signal-to-noise limitations of photon detectors used in diagnostic imaging systems. When fluorescent dye molecules are used as tracers for specific cells or structures, the signal conversion rates from illumination to fluorescence are very low and often buried in noise. In many therapeutic applications, such as PDT, the optical excitation of PDT labels on cancerous cells creates free radicals that kill nearby cells. Doses of intense optical illumination are applied to overcome the natural buffering mechanisms within the body, to attain effective concentrations of free radicals. Laser therapies that rely on optical heating, cutting, and cauterization of tissues require the highest optical intensities that can be delivered and cannot be used effectively with diffuse illumination. Directed, focused beams of light on tissue for precise exposure times are necessary for reducing surrounding tissue damage which is provided in a controlled optical scan system. Furthermore, high quality illumination can include a high degree of optical monochromaticity, coherence, polarization, high modulation frequency, high pulse repetition rates, and short pulse duration.

Figure 1C:
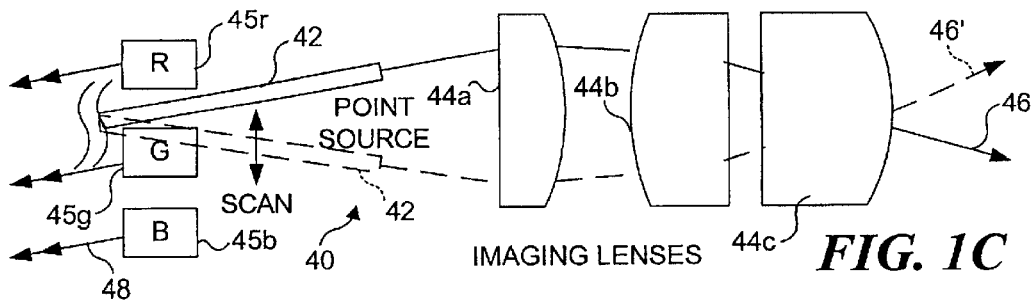
FIG. 1C is a schematic view of a scanning point-source illuminator with time-series photon detectors and imaging lenses in accord with the present invention.
Figure 1D:
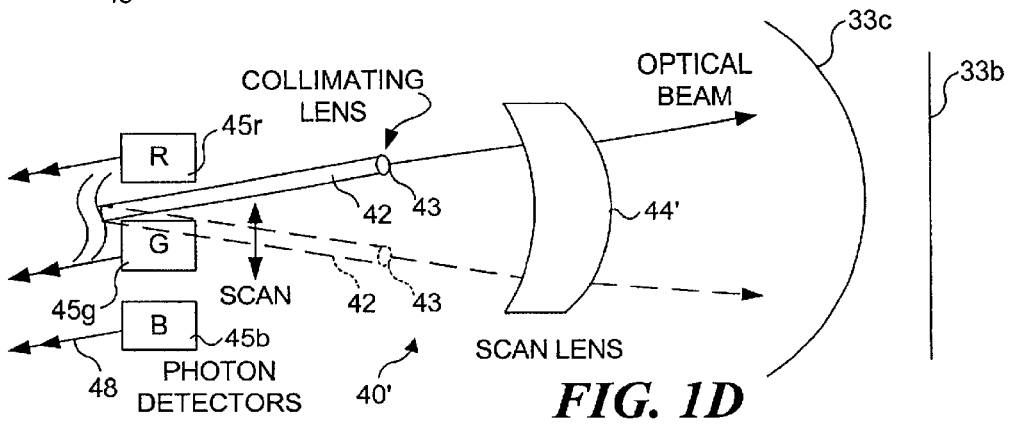
FIG. 1D is a schematic view of a scanning optical beam illuminator with a scan lens and detectors, in accord with the present invention.

FIGS. 1C and 1D illustrate embodiments of two-dimensional (2D) scanning point-source illuminators. In FIG. 1C, a scanning point-source illuminator 40 in accord with the present invention is illustrated. Point-source illuminator 40 has the capability of providing a point source illumination through an optical fiber 42 that is caused to scan an ROI within a patient's body. Light emitted by the scanning optical fiber is transmitted through imaging lenses 44a, 44b, and 44c to illuminate different portions of the ROI as the point source provided by the scanning optical fiber is caused to move. In the position illustrated with solid lines, a light beam 46 illuminates a particular portion of the ROI, while in the position illustrated by dash lines, the scanning optical fiber produces light beam 46' that illuminates a different portion of the ROI. Light reflected from each successive point illuminated by the scanning optical fiber is reflected back through imaging lenses 44c, 44b, and 44a and is received by RGB photon detectors 45r, 45g, and 45b, respectively, which produce corresponding electrical signals that are transmitted outside the patient's body for use in displaying a full color image of the ROI.

In addition, therapy can be rendered using scanning optical fiber 42. For example, by illuminating the points scanned by it using a relatively high powered laser, high intensity light PDT, or thermotherapy can be applied to the ROI. Since the signals produced by the RGB photon detectors correspond to successive points in the ROI, the image resulting from the signal that they produce is based upon a time series accumulation of image pixel data. Scanning optical fiber 42 is preferably a single mode or hollow optical fiber, of telecommunications grade or better. One significant advantage of this integrated system is that the mechanisms employed for generating the visual image are the same used for diagnostic, therapeutic, and surgical procedures. The method for imaging not only can match the image quality requirements for MIMPs, but can also achieve higher resolutions in a smaller package than existing imaging technology, so that a single, smaller, and more flexible system can be used for MIMPs. The relatively smaller scanning system reduces tissue trauma and expands the reach of MIMPs for use within adult, pediatric, and small animals. The directed optical illumination employed for image acquisition enables the most sophisticated diagnoses and therapies to be integrated into this single imaging system, (sharing the scan engine, display, and user interface). Integration may actually lower the cost of the equipment that would otherwise be required and/or decrease the time required to perform endoscopic MIMPs. The same benefits apply to each of the embodiments of the scanning system disclosed herein.

FIG. 1D illustrates a scanning optical beam illuminator 40' that also includes scanning optical fiber 42, just as the embodiment shown in FIG. 1C. However, instead of using imaging lenses, scanning optical beam illuminator 40' employs a collimating lens 43 that is attached to the distal end of the scanning optical fiber and a scan lens 44'. The light conveyed through optical fiber 42 is collimated by collimating lens 43 and then focused onto a flat illumination plane 33b, or a curved illumination plane 33c, each corresponding to the ROI within a patient's body. Light reflected from each successive point that is scanned as the scanning optical fiber moves passes back through scan lens 44' and is detected by RGB detectors 45r, 45g, and 45b, which respectively provide the RGB signals over lines 48 used to produce an image, with data accumulated pixel by pixel.

At the illumination plane, the beam of optical radiation is focused to achieve maximum intensity and/or optical quality, which is the goal for all modes of scanning. When tissue is coincident with the illumination plane, the optical irradiance is a function of the optical power and size of the light spot on the tissue. Thus, with regard to imaging, diagnoses, and therapy, the resolution of the MIMP is determined by this spot size at the image plane. With regard to image acquisition, the image resolution is determined by the illumination spot size, detector bandwidth (and scan rate), and signal-to-noise ratio (illumination intensity and collection efficiency), while image resolution is not limited by the physical size or number of the photon detectors.

Since diagnoses and therapies require accurate spatial discrimination, there is a need for directed illumination that is pre-calibrated before delivery. By integrating the optical imaging with diagnostic and therapeutic scanning, a medical practitioner can easily see the spatial discrimination of the optical scanning by viewing the displayed image before proceeding to diagnostic or therapeutic applications. Finally, the integration of computer image capture electronics and image processing software enables the image, diagnostic, and therapeutic data to be analyzed on a pixel-by-pixel basis. Since each pixel corresponds to the same area or volume of tissue, the single fiber integrated system maintains spatial registration for all three functions, imaging, diagnosis, and therapy. Consistent spatial registration from the same point of view for all three functions makes the single fiber system highly accurate and easy to use by medical practitioners of minimally invasive procedures.

The advantages afforded by using the integrated scanning device of the present invention for MIMPs are:
  Smaller size with integration;
  Lower cost with integration and use of low cost components;
  Lower flexural rigidity to allow greater access within the body;
  Faster procedural times, especially if requiring reiterations of therapy;
  Greater accuracy with integrated high-resolution imager and interactive display;
  Additional features with scanning optical system, such as variable resolution (real-time zooming) and enhanced stereo effects (such as shading);
  Additional functionality with integrated non-visible optical sources and detectors;
  Lower risk to patient for infection from multiple tools or multiple incisions; and
  Faster recovery times for patient with less healthy tissue damage and less anesthetics.

System Processing Overview

Figure 2:
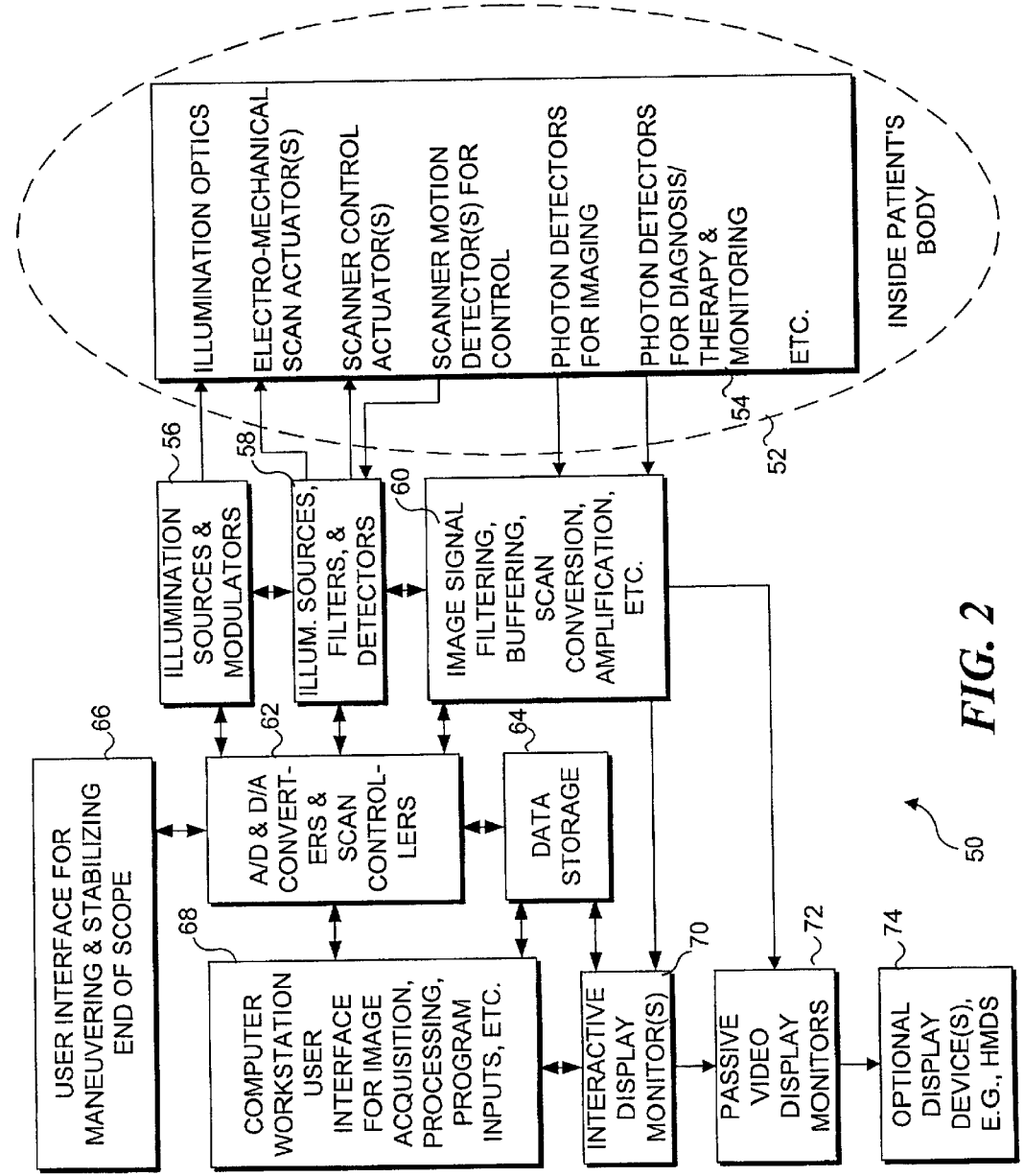
FIG. 2 is a block diagram illustrating the functional flow of signals in a system that is usable with an optical fiber for imaging, monitoring, rendering diagnoses, and providing therapy, in accord with the present invention.

FIG. 2 illustrates a system 50 that shows how the signals produced by various components that are inside a patient's body are processed with external instrumentation and how signals used for controlling the system are input to the components that are inside the patient's body. In order to provide integrated imaging and other functionality, system 50 is thus divided into the components that remain external to the patient's body, and those which are used internally (i.e., the components within a dash line 52). A block 54 lists the functional components disposed at the distal end of the scanning optical fiber system. As indicated therein, these components include illumination optics, one or more electromechanical scan actuator(s), one or more scanner control actuator(s), one or more scanner motion detector(s) for control of the scanner motion, photon detectors for imaging the ROI, and optionally, additional photon detectors for diagnostic purposes and for therapy and monitoring purposes. It should be noted that in regard to system 50, only the functional components actually required for a specific application may be included. Also, the additional functions besides imaging can be diagnostic, or therapy, or a combination of these functions.

Externally, the illumination optics are supplied light from illumination sources and modulators as shown in a block 56. Further details concerning several preferred embodiments of external light source systems for producing RGB, UV, IR, and/or high intensity light conveyed to the distal end of an optical fiber system are disclosed below. A block 58 indicates that illumination sources, modulators, filters, and detectors are optionally coupled to the electromechanical scan actuator(s) inside the patient's body and to the scanner control actuators. Scanner motion detectors are used for controlling the scanning and produce a signal that is fed back to the scanner actuators, illumination source, and modulators to implement scanning control.

In a block 60, image signal filtering, buffering, scan conversion, amplification, and other processing functions are implemented using the electronic signals produced by the imaging photon detectors and for the other photon detectors employed for diagnosis/therapy, and monitoring purposes. Blocks 56, 58, and 60 are interconnected bi-directionally to convey signals that facilitate the functions performed by each respective block. Similarly, each of these blocks is bi-directionally coupled in communication with a block 62 in which analog-to-digital (A/D) and digital-to-analog (D/A) converters are provided for processing signals that are supplied to a computer workstation user interface employed for image acquisition, processing, for executing related programs, and for other functions. Control signals from the computer workstation are fed back to block 62 and converted into analog signals, where appropriate, for controlling or actuating each of the functions provided in blocks 56, 58, and 60. The A/D converters and D/A converters within block 62 are also coupled bi-directionally to a block 64 in which data storage is provided, and to a block 66. Block 66 represents a user interface for maneuvering, positioning, and stabilizing the end of the scanning optical fiber within a patient's body. Further description of a system for providing the stabilizing functions performed in this block are discussed below.

In block 64, the data storage is used for storing the image data produced by the detectors within a patient's body, and for storing other data related to the imaging and functions implemented by the scanning optical fiber. Block 64 is also coupled bi-directionally to the computer workstation and to interactive display monitor(s) in a block 70. Block 70 receives an input from block 60, enabling images of the ROI to be displayed interactively. In addition, one or more passive video display monitors may be included within the system, as indicated in a block 72. Other types of display devices, for example, a head-mounted display (HMD) system, can also be provided, enabling medical personnel to view an ROI as a quasi-stereo image.

Cantilevered Scanning Optical Fibers

A "zigzag" or rectilinear scanning optical fiber 80 is shown in FIGS. 3A and 3B. The scanning optical fiber includes a stationary mechanical support portion 82 that is biocompatible or has a bio-compatible coating 84 surrounding a mechanical base 86. Extending from the distal end of mechanical base 86 is a bimorph piezoelectric bender 88, which responds to an electrical voltage applied across its opposite faces by bending in opposite directions, as indicated by an arrow 96. A plurality of photon detectors 92 are arrayed around a central cantilevered optical fiber or waveguide 94 and are mounted on a secondary support disk 93. Cantilevered optical fiber 94 is caused to move in the direction indicated by an arrow 98 by a tube piezoelectric actuator 95 through which the optical fiber extends. A plurality of electrical leads 90a and 90b extend along the sides of bimorph piezoelectric binder 88 and convey signals from the plurality of photon detectors to components disposed outside the patient's body as shown in system 50 of FIG. 2. As noted in FIGS. 3A and 3B, arrows 96 and 98 are substantially orthogonal to each other, enabling the scanning of cantilevered optical fiber 94 to be implemented in a zigzag or rectilinear manner so that an ROI can be scanned by row and by column. Not shown is the overall enclosure containing the biocompatible sleeve and distal lenses.

The zigzag or rectilinear embodiment shown in FIGS. 3A and 3B is less preferred than other embodiments disclosed below, because of its substantially larger physical size and the required movement of the photon detectors. For example, cantilevered optical fiber 94 is typically approximately 0.1 mm in diameter, and the overall diameter of stationary mechanical support 82 can be several millimeters in diameter.

Scanning actuators other than piezoelectric actuators can be employed to cause an optical fiber to move in a scanning mode. For example, FIG. 3C illustrates a scanning optical fiber driver 100 that includes a cantilevered optical fiber 102 having a ferrous bar 103 attached to one side so that an electromechanical actuator 110, when energized with an electrical current flowing through a coil 112 that is wound around a core 114 attracts the ferrous bar, causing the optical fiber to scan in a 2D manner, as indicated in the Figure. Preferably, the scanning optical fiber is driven at one or more frequencies that are harmonics of its resonant frequency, to achieve optimum efficiency. However, it is also contemplated that the optical fiber can be driven at a non-resonant frequency. Although not shown, a second electromechanical actuator can be included to provide a force in a direction orthogonal to that of electromechanical actuator 110 to cause cantilevered optical fiber 102 to scan in a direction orthogonal to that indicated in FIG. 3C. Thus, by controlling the current supply to each of an orthogonal pair of electromechanical actuators, the scan position of cantilevered optical fiber 102 can be precisely controlled.

The cantilevered optical fiber emits light that passes through an imaging lens 104 and is focused on an imaging plane 106 corresponding to the ROI within a patient's body, producing a PSF 108 as indicated. As the cantilevered optical fiber is caused to move by electromechanical actuator 110, a PSF 108' is formed at a different location on imaging plane 106.

In FIG. 3D, yet another embodiment 120 is illustrated in which a scanner 122 comprises an electromechanical device or piezoceramic tube actuator that causes a first mode of vibratory resonance in a cantilevered optical fiber 124. In this case, the cantilevered optical fiber includes a collimating lens 126 at its distal end and a scan lens 128 that re-images light that has passed through the collimating lens, onto an illumination plane 132. Light focused by scan lens 128 forms a PSF 134 on illumination plane 132 and as the cantilevered optical fiber moves, a PSF 134' moves over the illumination plane. Although cantilevered optical fiber 124 can be limited to scanning along a single axis as indicated by arrows 130, it is also possible to use an actuator that moves the optical fiber so that it scans along an orthogonal axis (i.e., in and out of the plane of the drawing figure). However, at high amplitude resonance vibration driven by a linear single axis actuator, the resulting motion of the optical fiber can be in two dimensions due to nonlinear cross-coupling of mechanical forces. Thus, two axis actuators are not required for 2D scanning.

Scanning Thin Film Light Waveguide Embodiments

It should be apparent that it is desirable to produce a scanning optical fiber with a smaller cross-sectional area than that shown in the embodiments of FIGS. 3A and 3B and also to produce such a device at relatively low cost and volume to make these devices more economical and thereby facilitate their widespread use as disposable devices. Microelectromechanical systems (MEMS) technology enables these goals to be achieved using a thin film device with integrated actuators. FIGS. 4A, 4B, and 4C illustrate an early prototype of a thin film optical system 140, in which this approach was shown to be effective. A further alternative 140' illustrated in FIG. 4D includes parallel cantilevered thin film optical waveguides for scanning and detectors. While it is likely that a production version of the thin film imaging system illustrated in these figures will be more compact and more suitable for volume production, the early prototype at least proves that the thin film optical device has an effective scanning capability and is usable in the present invention.

In the thin film optical device, an optical fiber 144 having a cladding 142 is actuated using an electrostatic actuator 156. However, in this case, instead of causing an optical fiber to scan, electrostatic actuators 156 act on a thin film optical waveguide 150 that is supported on a raised ledge 148. A distal portion 152 of the thin film optical waveguide is thus caused to scan in the two orthogonal directions indicated by the curved arrows in FIGS. 4A and 4B. The thin film optical waveguide is only approximately 0.005 mm in diameter. It should be noted that the scanning motion can be one-dimensional (i.e., along a single axis), or as shown, in two dimensions (along a raster pattern). Optionally, the thin film optical device can be mounted on a rod 143, which is then manually or mechanically rotated or vibrated to change the orientation or displace the single axis scan. Also provided is a lens 154 that is preferably mounted to a silicon substrate 146 (or other substrate material). As an alternative, external actuators (not shown) can be used instead of the electrostatic actuators, in which case, optical fiber 144 and lens 154 would be supported by silicon substrate 146, which would be caused to vibrate by the external actuators, causing the cantilevered thin film optical waveguide to resonantly scan. Optical fiber 144 is preferably affixed to silicon substrate 146 within a centering V notch 160 to ensure that it is aligned with thin film optical waveguide 150. Since the optical fiber is approximately 0.1 mm in diameter, care must be taken to provide accurate alignment between the ends of the optical fiber and the thin film optical waveguide.

FIGS. 4A and 4B shows the embodiment using butt-end coupling between optical fiber 144 and a thin film optical waveguide 150. To ensure appropriate alignment between the optical fiber and the thin film optical waveguide, V notch 160 precisely establishes a disposition of the optical fiber relative to the thin film optical waveguide. In the view of the embodiments shown in FIGS. 4A, 4B and 4C, light reflected back from an ROI passes through lens 154 and is received by RGB detectors 162r, 162g, and 162b, respectively. These detectors respond to the light of the corresponding color, producing a signal that is conveyed proximally to the external components, as discussed above. In FIG. 4D, separate image and diagnostic/therapeutic thin film optical waveguides are spaced apart and scanned in parallel; this embodiment uses a diagnostic "DIAG" detector 162d.

Tapered and Other Scanning Optical Fibers

Other techniques can also be used to produce a relatively small illumination PSF. For example, as shown in FIGS. 5A and 5B, a conventional optical fiber 164 includes a micro-fabricated end 168 with a taper 166. The micro-fabricated end is formed either by etching (most preferable), micro-machining, or by pulling a heated optical fiber and then cutting the pulled fiber at its desired reduced diameter (least preferable). By chemically etching the cladding layer to a minimum thickness at the distal tip, the tapering produces no optical transmission losses. Since there are usually optical transmission losses associated with reducing the optical fiber source size during a pulling process, a reflective coating 167 can optionally be applied to the sides of the tapered waveguide. However, these procedures can be combined to generate a micro-fabricated optical fiber scanner with increased scanning frequency, FOV, and resolution. One advantage of using a scanning optical fiber having micro-fabricated end 168 is that the resonant frequency of the optical fiber shown in FIG. 5B is substantially greater than the resonant frequency of a blunt tip optical fiber that has not been micro-fabricated. However, the major advantage is the generation of much greater amplitude of tip deflection at this higher resonant frequency compared to untapered fibers. As mentioned above, the distal motion of micro-fabricated end 168 can produce linear patterns 169a and two-dimensional patterns 169b. Furthermore, the larger tip deflection has smaller lateral tip displacement, compared to optical fibers that have not been micro-fabricated. The etching process that is preferably used to produce the micro-fabricated tapered end is carried out using techniques well known to those of ordinary skill in the art.

As shown in FIG. 5C, the relative PSF and FOV of various forms of optical fibers varies depending upon the nature of the site at the distal end of the optical fiber from which the light travels toward an ROI 170. Displacements of specific optical fibers in the vibrational first, second, and third modes of resonance are indicated by dash lines in this Figure. An optical fiber 172 having a blunt end is driven to vibrate about in a single axis in a first resonance mode and emits light 174 focused by a lens 184, producing a PSF 176, which is the widest due to the larger size of the site at the distal end of the optical fiber. A PSF 182 that is the smallest is produced by light 180 from a tapered optical fiber 178 (either etched, micro-machined, or pulled as discussed above), which is driven in a higher resonance mode along a single axis. It should be noted that the physical scan distance through which this tapered optical fiber vibrates in resonance is relatively small, enabling it to be encased within a small diameter housing. Light 188 from an optical fiber 184 that is coupled to a ball lens 186 at its distal end and driven in the second mode (with a node in the ball lens) provides light that passes through a lens 185, producing an intermediate size PSF 190 covering the greatest FOV of the three configurations. The second and third mode embodiments exhibited in FIG. 5C are generally preferred because they require only a single actuator, they are relatively small in cross-sectional size, and they provide relatively high resolution, while enabling versatile scanning of an ROI.

Other modes of scanning can also be achieved that differ from the linear mode, or the rectilinear or zigzag mode noted above. FIG. 5D illustrates a variable radius or spiral scan mode of an optical fiber scanning system 200, which can be generated by a two axis piezoceramic tube actuator 206. In this embodiment, a plurality of light detectors 204 are arrayed around single piezoceramic tube actuator 206 in a simple arrangement, to produce signals indicative of the light received from an ROI (not shown in this Figure). Alternatively, a similar array of concentrically arranged and spaced-apart optical fibers 202 can convey light received at the distal end of the optical fibers from the ROI to light detectors (not shown) at a proximal end of the optical fibers (e.g., outside the body of a patient). Piezoceramic tube actuator 206 concentrically surrounds a clad optical fiber 208 that is tapered to a distal end 210. This tube actuator produces a driving force corresponding to a harmonic of a natural resonant frequency of optical fiber 208 so that the distal end of the optical fiber produces an orbit 212 having an actuation controlled radius. At the distal end of the scanning optical fiber is the optical point source, which can be focused out to an illumination plane (not shown) by adding an imaging lens (not shown). The major advantages of this embodiment over the other embodiments discussed hereinabove are that this embodiment employs a single actuator and a tapered waveguide that provide high resolution, directed illumination, and imaging within a relatively small diameter enclosure.

A series of variable radii circles are produced in a circular scan mode, while in a spiral scan mode, the optical fiber produces a spiral scan in which the radius alternately increases and decreases. In either the circular or spiral scan modes, the distal end of optical fiber 208 scans an ROI to image the region and also renders therapy and/or diagnostic functions over the ROI. The whirling motion of the cantilevered optical fiber is controllably driven larger or smaller in diameter by increasing or decreasing the voltage applied to the four individual quadrants of piezoceramic tube actuator 206. A "propeller" scan mode 216 is illustrated in FIG. 5E. In this scanning mode, the scanning optical fiber moves back and forth along different diameters of a circle, scanning the ROI. The rotation of the linear scan can be generated from the two axis piezoceramic tube actuator or by simply rotating a single-axis actuator about the longitudinal axis of the optical fiber.

To achieve a maximum numbers of pixels across the widest FOV, for imaging, diagnosis, and therapy, a diffraction-limited spot of illumination must be formed by the lens system. Assuming an ideal scanning optical fiber, the spatial resolution of the delivered illumination is limited by the projected optical point source size and the diffraction-limited or aberration-limited performance of the lens system. When an optical system is aberration-limited, the main purpose of a secondary imaging lens or a small lens 228 at the fiber tip in FIG. 5F is to reduce optical aberrations and thus to reduce the illumination spot size. In a diffraction-limited optical system, a smaller spot size is achieved with larger lenses or beams of scanned optical illumination. Thus, high-resolution optional designs will use an oversized collimating lens or a ball lens 245 for increasing pixels within a fixed FOV, as shown in FIG. 5H. Assuming a diffraction-limited collimation and scan lenses, a maximum number of pixels or display resolution is theoretically possible for an optical fiber scan system that is within about a 1.0 mm diameter enclosure. Note that the lateral vibratory resonance mode depicted in FIGS. 5F and 5H satisfies the requirement of high angular deflection at the distal tip without large lateral displacements of the moving waveguide. By scanning in a whirling or propeller motion, this embodiment can provide both high resolution and a wide FOV in an ultrathin single fiber system.

FIG. 5F thus illustrates details of a beam scanning embodiment 220, which is perhaps the most preferred of the embodiments thus far discussed. It will be recalled from FIG. 5C, which was discussed above, that use of the ball lens on the distal end of the optical fiber produces a PSF that is consistently small across a wider FOV than the other forms of scanning optical fibers, and thus, has a relatively small spot size 240, as indicated in FIG. 5G. Beam scanning embodiment 220 includes a cylindrical supporting housing 222 in which is disposed a cylindrical actuator 224 of the piezoelectric or piezoceramic type that drives an optical fiber 226 to vibrate in a resonant 2D scanning mode so that the optical fiber bends to form nodes on opposite sides of the nominal longitudinal axis of the device (as discuss further below in regard to the example shown in FIG. 5H). A ball lens 228 is affixed to the distal end of optical fiber 226. Light conveyed through the optical fiber is focused forming a beam 230 by the ball lens and by a lens 238. Beam 230 describes an angle that is preferably greater than or equal to at least 40° relative to the longitudinal axis of the optical fiber and of cylindrical housing 222. When scanning, the center of the cantilevered portion of the optical fiber moves back and forth about this axis, as illustrated, while a center of ball lens 228 remains generally stationary due to its inertial mass and the fact that the vibratory node is near the tip at the second node of resonance (see FIG. 5C). The length of optical fiber 226 extending distally beyond actuator 224 and the mass of ball lens 228 are selected to ensure that the scanning occurs with this form of motion. Light detectors 232 are disposed around cylindrical actuator 224, which may be coated with high reflective material (e.g., aluminum) 237 to help channel the backscattered light to the detectors at high efficiencies.

Theoretically, only a single light detector is required to collect the backscattered scanned light, to generate a monochrome or black and white image. A simple method for generating a full-color image is to use three light detectors (as noted above), each covered with a different filter selected for blue, green, or red light transmission. Silicon-based semiconductor photodiodes (such as Si-PIN type) are preferred for visible and near IR light detection because of their high sensitivity, low cost, small size, high speed, and ruggedness. Photodiodes used routinely in the telecommunications industry, such as InGaAs material photodiodes, are preferred for embodiment of the present invention that use IR optical detection. Since the resolution of the integrated optical scanning technique does not depend on size and number of light detectors, all available space at the distal end of the optical fiber assembly can be covered with light detectors for the purpose of increasing and discriminating between signal levels. As will be more apparent from the discussion that follows, the light detectors are preferably provided in stereo-pairs about the optic axis so that topographical features (e.g., shadows) of the ROI can be enhanced and glare from spectral reflections can be diminished. If IR radiation is used in conjunction with visible light, then light detectors of different light-sensitive materials can be used without filters (not shown). An alternative method for separating the spectral response of a light detector that is not filtered requires synchronizing the detector signal in time with an appropriate illumination source having a pulsed output. For example, the same visible light detector can be used without any filters if the RGB laser or other light sources are individually pulsed in rapid time series and in synchronicity with the processing of signals received from the light detectors.

Leads 234 extend from each of the light detectors to the proximal end of the optical fiber, which is external to the patient's body, to convey the electrical signals from the light detectors to the external instrumentation, as discussed above. Actuator 224 is driven with an electrical signal supplied through leads 236.

Further details helping to explain the motion of an optical fiber 244 that is driven into vibration by an actuator such as actuator 224 are shown in FIG. 5H for an oversized collimation lens, which provides higher resolution in a relatively small package. Optical fiber 244 is surrounded by cladding 242 and at its distal end, is coupled to ball lens 245 that collimates the light traveling through optical fiber 244. As noted above, due to its relatively larger mass, ball lens 245 remains substantially stationary, while the center of the cantilevered portion of optical fiber 244 deflects upwardly and then downwardly. Light traveling through optical fiber 244 passes through a center 246 of ball lens 245 as the optical fiber moves between the upper and lower range of the scan as illustrated. Light passing through ball lens 245 exits a scan lens 248 with a collimation diameter of approximately 0.5 mm. At its maximum amplitude of vibration, optical fiber 244 describes an included angle that is approximately 60° around center 246 in ball lens 245. Thus, the light emitted that travels through scan lens 248 has a relatively small PSF or spot size as it scans an ROI. This oversized ball lens embodiment is described in "Single Fiber Flexible Endoscope: General Design for Small Size, High Resolution, and Wide Field of View," Eric J. Seibel Quinn, Y. J. Smithwick, Chris M. Brown, and Per G. Reinhall, Biomonitoring and Endoscopy Technologies, Proceedings of SPIE, Vol. 4158 (January 2001), the disclosure of which is hereby specifically incorporated herein by reference. The embodiment with a lens at the distal end of the optical fiber can use a gradient index lens, diffractive or optical element, or combination of diffractive and refractive lenses.

Optical Fiber Systems for Imaging and Spectral or Polarized Light Analysis

FIG. 6A illustrates a system 266 that is used for providing both a quasi-stereo image of an ROI and for acquiring a spectral image that can be analyzed with a spectrophotometer, in accord with the present invention. In this system, an optical fiber assembly 250 includes an optical fiber 256 that is tapered at its distal end and is surrounded by a piezoelectric actuator 254. Actuator 254 causes optical fiber 256 to vibrate and scan an ROI, emitting light that passes through lenses 258a and 258b. Light reflected from the ROI or light otherwise received therefrom (such as phosphorescent or fluorescent emissions) is collected by twelve optical fibers 252 that are arranged in a circumferential array around optical fiber 256. As illustrated in this exemplary figure, optical fibers 1, 2, and 3, which are collectively referred to by a reference number 260, are respectively coupled to external RGB imaging detectors corresponding to a left side of the circumferential array. Similarly, optical fibers 7, 8, and 9, which are collectively identified by a reference number 262, are respectively coupled to a RGB imaging detectors for the right side of the circumferential array. Another set of optical fibers 264 corresponding to optical fibers 4, 5, 6, 10, 11, and 12 are coupled to a spectrophotometer 270. The spectrophotometer is employed for spectral analyses and spectral image acquisition using UV, visible, and/or IR light. Since the RGB detectors for the left and right side of the circumferential array receive light from the ROI at two spaced-apart portions of the array (i.e., the left and right sides), they produce a quasi-stereo full color image that is readily viewed using an HMD display (not shown).

Another system 271 in accord with the present invention is illustrated in FIG. 6B. In system 271, an optical fiber bundle 250 is arrayed concentrically around optical fiber 256 and is coupled to a spectrophotometer 272 that uses a prism/grating and an array of spectral detectors to measure the spectra of light received from the ROI. The output signals from spectrophotometer 272 are input to a computer workstation and spectrum analyzer 274, which produces a full color image on an RGB video display 276. Also, computer workstation and spectrum analyzer 274 is connected to a spectral display 278 that can be employed for spectral analysis and diagnoses of the ROI. An integrated display of both a standard endoscopic image and spectral mapping, and any additional diagnostic/screening information can be shown together in a multitude of modalities 279, such as text, pseudo-color overlays, audio enhancement, stereoscopic viewing, etc. As in system 266, a portion of the optical fiber system that is disposed within a patient's body is indicated within a dash line rectangle.

To control optical fiber scanning, additional light detectors and emitters can be employed adjacent (along or adjacent) to the scanning optical fiber to detect the motion and position (or frequency and speed) of the optical fiber distal tip over time. As shown in FIG. 6A, the increase in light leakage incurred when the optical fiber makes a sharper bend can be detected using passive photon sensors 255.

In FIG. 6B, an IR emitter 281 and an IR detector 283 are located on opposite sides of the optical fiber scanner and use the change in optical light transmission caused by the changing position of the vibrating tapered distal end or tip of the optical fiber 256 to control the tip position. In FIG. 6C, emitter 281 and detector 283 are disposed adjacent (alongside) each other and are used to detect a change of reflected light. These methods are routinely used in the optical fiber sensing industry (although not for controlling scanning), and emitters and detectors of separate, non-imaging wavelengths are especially useful in controlling scanning probe microscopes. The signals from these sensors, which can also be piezo-electrically, magnetically, or electrostatically based, are used in feedback controllers that increase scanning rates, while reducing scanner distortion.

Spatial resolution of the scanning optical fiber system that produces directed illumination for therapy depends on the number of distinguishable spots of light that can be projected onto the illumination image plane. The resolution depends on the minimum spot size while FOV depends on the maximum scan angle (total number of distinguishable spots). When acquiring images, spatial resolution also depends on the bandwidth of the photon detectors, (assuming sufficient signal-to-noise ratio), and the total number of pixels available in the display system. By operating within bandwidth limitations of the scanning system components, the resolution and FOV can be changed dynamically, enabling features such as zooming or dynamic magnification of the ROI. In many applications, both the ROI and the single optical fiber system are stationary (other than the scanning distal end of the optical fiber), reducing the likelihood of introducing any blurring from scanning well below the refresh rate of the display device. By scanning slower than standard video rates, the optical system can deliver higher power levels for optical therapies and allow longer times for signal integration from weak-signal fluorescence diagnoses. Thus, the dynamic range of the scanning optical system can be optimized according to the system components and application requirements.

Illumination may only occur in one or a few pixels per frame. For example, real-time optical biopsies can be carried out with the present invention at single points in an ROI, enabling very bright flashes of light excitation to be used and providing time for spectroscopic acquisition and spectral mapping over the normal image.

FIG. 6C illustrates a portion of a concentric optical fiber assembly 280 that includes a relatively small central optical fiber 284 surrounded by cladding 286. A larger diameter optical fiber surrounds the smaller optical fiber. Illumination of an ROI is provided through small diameter optical fiber 284, and light emitted thereby passes through lenses 288*a*, 288*b*, and 288*c* to illuminate the ROI. Light reflected or otherwise received from the ROI is focused by these lenses back into an optical fiber assembly 289, which conveys the light that is received to instrumentation disposed outside the patient's body. It should be noted that a single optical fiber can both illuminate the ROI and convey light from the ROI to the external instrumentation in this so-called concentric confocal imaging. The concentric optical fiber geometry is a single mechanical unit either fused together, or alternatively, the concentric regions of refractive index differences can be manufactured by doping the glass fiber radially. A tubular piezoelectric actuator 282 causes the concentric optical fibers to move together and thus to scan the ROI in one of the modes described above. The light collected in the surrounding optical fiber can be used with signals from detectors or optical fibers at radially increasing distances from the reflected confocal point to enhance image analysis and refine the depth of light penetration for diagnosis, imaging, and therapy. In extremely high-gain or discrimination detection configurations, the backscattered light may be collected in the same part of the waveguide (e.g., the core of the optical fiber). Such applications will use the optical coherence property to amplify the small signal level, producing diagnostic maps based upon optical coherence reflectometry (OCR) or optical coherence tomography (OCT), or laser-induced feedback.

FIGS. 6D and 6E illustrate an embodiment that includes detectors for RGB, UV, and IR spectral components. An optical fiber assembly 295 includes an internal actuator 291 mounted on a support 293. An optical fiber 300 enclosed within the housing having an opening 298 extends distally of actuator 291 and is moved by the internal actuator, which is preferably a tubular piezoelectric type, in one of the modes described above. RGB detectors 292 and 294 are disposed above and below optical fiber 300, while RGB detectors 306 and 308 are disposed to the left and right of the optical fiber, as illustrated in FIG. 6E. In addition, RGB detectors 290 and 296 are disposed on the outer surface of the assembly on the top and bottom thereof, as indicated in these Figures. In a similar manner, RGB detectors 302 and 304 are mounted on the left and right sides of the detector as illustrated in FIG. 6E. UV detectors 310 and 312 are mounted on one of the diagonals between the RGB detectors, while IR detectors 314 and 316 are mounted on the other diagonal. Accordingly, a quasi-stereo image can be produced in regard to the RGB, UV, or IR spectral components received by the various detectors included on this assembly.

FIGS. 6F and 6G illustrate an optical fiber assembly 295' in which parallel and perpendicular polarized light detectors are included. Optical fiber 300 conveys light that is polarized in a parallel direction as indicated by reference numeral 328. On opposite sides of optical fiber 300 are disposed parallel polarized light detectors 334 and 336, while above and below optical fiber 300 are disposed perpendicular polarized light detectors 324 and 326, as shown in FIG. 6G. In addition, perpendicular polarized light detectors 320 and 322 are disposed above and below perpendicular polarized detectors 324 and 326, while parallel polarized light detectors 329 and 330 are disposed left and right of parallel polarized light detectors 334 and 336. Optical fiber assembly 295' is thus able to detect polarized light in both orientations that is reflected or otherwise received from an ROI for analysis by instrumentation disposed external to the patient's body. The signal produced by the various polarized light detectors can also be used for producing an image corresponding to that specific type of polarization.

A schematic diagram illustrating a light source system 340 for producing light of different spectral composition that is coupled into an optical fiber 360 is illustrated in FIG. 7A. In this embodiment, a red light source 342, a green light source 344, a blue light source 346, and an UV light source 348 are each selectively coupled into optical fiber 360. Attenuators 350 are provided for each of the light sources so that the intensity of the light they produce can be selectively controlled. Three dichroic mirrors 352, 354, and 356 that include coatings specific to the color of light emitted by each of the corresponding green, blue, and UV light sources are positioned within the light path to reflect green, blue, and UV light, respectively, into the proximal end of optical fiber 360. Light that is outside the reflectance waveband for each of these dichroic mirrors is passed through the dichroic mirror and is focused by a lens 358 into the proximal end of optical fiber 360.

An alternative light source system 362 is illustrated in FIG. 7B. In this embodiment, red, green, and blue light sources 342, 344, and 346, respectively, are coupled through optional attenuators 350 to a series or sequence of optical couplers 366 through lenses 364. Lenses 364 focus the light from each of the different colored light sources into optical fibers 365, which convey the light to optical couplers 366. In addition, an IR source 368 transmits light through an optional attenuator 350 and a lens 364 into optical fiber 365, which conveys the IR light to the last optical coupler in the sequence. Optical detectors 370 are provided for monitoring the light intensity levels or power levels for each of the different sources of light, enabling the intensity of the various light sources to be controlled. From the last optical coupler, an optical fiber 367 conveys light to an input to optical detectors 370, while the output from the last optical coupler is input to the proximal end of optical fiber 360 for input to a patient's body. To produce the smallest affective source size, the optical fiber that would be chosen in FIG. 7C would be single mode for wavelengths at or above that of blue light.

A multi-spectral component laser light source system 380 is illustrated in FIG. 7C. In this system, a tunable wavelength IR laser 382 produces IR light that passes through an optional frequency multiplier 384 and into a shutter and power meter 386. The shutter and power meter can be controlled to modulate the intensity of the IR light and also to control whether it is applied to the proximal end of an optical fiber 402 that leads into a patient's body. Alternatively, tunable wavelength IR laser 382 can be frequency multiplied to emit shorter wavelength light. In addition, a green laser 388 produces green coherent light that passes through one of a plurality of shutters 390, while a blue laser 392 produces blue coherent light also controlled by a shutter 390. Similarly, a red laser 396 produces red coherent light. A plurality of dichroic reflectors 394 are used to convey the light from the various laser sources through a lens 398, which focuses the light into a tapered hollow glass tube 400. The angle of the taper of the tapered hollow glass tube is such that internal reflections on its inner surface cause the light from each of the laser sources to be "funneled" into the proximal end of optical fiber 402. The funneled light of combined wavelengths can be transferred to a solid core or hollow core optical fiber for delivery to the tissue in the ROI at the distal end of the optical fiber. Although the light from each of the laser sources might well be of relatively high intensity for therapeutic or diagnostic purposes, tapered hollow glass tube 400 is easily capable of combining the high powered signals from the laser sources. Further details of the hollow glass funnel are provided in a paper entitled "Ultraviolet, Visible, and Infrared Laser Delivery Using Laser-To-Fiber Coupling Via a Grazing-Incidence-Based Hollow Taper," by I. Ilev and R. W. Waynant, from the proceedings of the EOS/SPIE/ELA European Biomedical Optics Week—EbiOS 2000, Amsterdam, the Netherlands, Jul. 4, 2000. This paper will also be published in 2001 as Volume 4158 of the "Proceedings of the SPIE, Biomonitoring and Endoscopy Technologies." Also see "Uncoated Hollow Taper as a Simple Optical Funnel for Laser Deliver," by I. Ilev and R. W. Waynant, Review of Scientific Instruments, Vol. 70, No. 10, pp. 3840–3843 (1999).

Functional Block Diagrams

FIG. 8 illustrates the variety of functions that can be carried out with the present invention. Functions such as diagnosis, therapy, and monitoring are shown in blocks that are formed with dash lines, while solid lines are used for imaging functions of a system 410. As illustrated therein, imaging lasers 412 produce light that is directed into a patient's body and through imaging optics on the scanning optical fiber. Furthermore, diagnostic, therapeutic, and monitoring lasers in a block 416 that are controlled by a remote optical switch and attenuators in a block 418 produce coherent light conveyed through an optical coupling mechanism 420 to additional optical components 422 disposed inside the patient's body. RGB photon detectors 430 respond to light received from the ROI, producing an electrical signal that is conveyed through electrical conductors to instrumentation disposed outside the patient's body. Alternatively, the RGB light can be conveyed through optical fibers to external photon detectors 426 or to other types of optical detectors 424 that include, for example, photodiodes and related circuitry. As indicated in a box 432, the system may include additional high or low power UV, and/or visible, and/or IR detectors associated with collection optical fibers for use by one or more spectrophotometers or spectrum analyzers. For example, spectrophotometers and spectrum analyzers indicated in a block 434 can receive light conveyed through light collection optical fibers and/or as signals conveyed over conductors as indicated in a block 436. The system may include additional photon detectors disposed inside the patient's body as a further option. Signals are exchanged bi-directionally between block 432 and 434 and a computer workstation and data acquisition component in a block 440. The computer workstation can execute algorithms that provide for non-linear scanning patterns and control algorithms and also can be programmed to carry out intensity data acquisition, image mapping, and storage of data. In addition, tasks including real-time filtering (e.g., correction for motion and scanner artifacts), real-time determination of ratios and background subtraction, deconvolution, quasi-stereo enhancement, and processing of the signals produced by the various detectors are implemented by the computer workstation. Signals provided by the computer workstation are output to image display devices and data storage. The image display devices may include cathode ray tube, liquid crystal displays, and HMD devices or other types of stereographic displays, as noted in a block 442. The integrated single fiber system can be applied more easily in future minimally invasive telesurgical and robotic procedures, because of its ability to convey 3D views and to enable a hands-off operation. Since commercially available displays for MIMPs require rectilinear video format, any non-rectilinear optical scanning patterns must be stored in data buffers (memory) and converted to the standard raster scanning format for the display monitors, to make use of the many advantages of non-rectilinear scanning, (such as a simplified single actuator, cylindrical scanner size, and lower scanning rates). This additional step in signal conditioning and remapping is technically trivial with programmable memory devices.

In addition, image analysis software for carrying out spectral and multivariate analysis and for locating and calculating the limits of regions of interest are carried out using the computer workstation or other computing device. In regard to the ROI, the computations may determine its distribution, boundary, volume, color, and optical density, and based upon the data collected from the ROI, can determine a tissue disease state, medical staging, as well as calculate and monitor therapeutic dosage. All of these functions are indicated in a block 444, which may use the normal imaging computer workstation of block 440. Block 444 is coupled to a block 446, in which additional interactive displays and image overlay formats are provided. Associated with block 444 is a block 448, which indicates that scanner power and control electronics are provided for actuating the electromechanical scanner and for receiving signals from servo sensors in a block 450, which are used for both normal image acquisition and enhancements involved in screening, monitoring, and diagnosis, as well as pixel accurate delivery of therapy.

Various embodiments of optical fiber scanning actuators have been described above. A block 454 indicates that provision is made for manual control of the distal tip of the scanning optical fiber, to enable the optical fiber to be inserted into a patient's body and positioned at a desired location adjacent an ROI. The manual control will include a turning device and servo sensors, as indicated in a block 456 to facilitate the introduction of the scanning optical fiber at the desired location. Once positioned, automatic vibration compensation is provided, as noted in a block 452 to stabilize the image in regard to biological motion (breathing and cardiovascular movement) and physical movement of the patient. In addition, other mechanisms are provided in at least one embodiment that is disclosed below for stabilizing the optical fiber where desired within a body cavity or passage within a patient's body.

Details of the various functions that can be implemented with the present invention as follows:

Integrated Imaging, Screening, and Diagnosis

Optical tissue imaging using UV, visible, and IR wavelengths;

Fluorescence imaging using UV, visible, and IR wavelengths;

Thermal imaging using IR wavelengths;

Deep tissue imaging using IR wavelengths;

Concentric confocal and true confocal imaging;

Imaging through blood using IR wavelengths;

Polarization-contrast imaging;

Laser feedback microscopy;

Optical coherence tomography (OCT) and reflectometry (OCR);

Optically stimulated vibro-acoustography analysis;

High resolution and magnification tissue-contact imaging;

Laser-induced fluorescence (LIF) and ratio fluorescence imaging and detection;

Multi-photon excitation fluorescence imaging;

Fluorescence lifetime imaging and analysis;

True sizing of imaged structures using stereo and range finding options;

Laser-induced fluorescence spectroscopy (LIFS);

Raman spectroscopy analysis;

Elastic scattering spectroscopy (ESS) analysis;

Absorption spectroscopy;

Detection and mapping of chemi-luminescence and cell viability;

Spatial mapping of optical sensor data (oxygen concentrations, pH, ionic concentrations, etc.);

Temperature measurement and feedback control; and

Other measurements such as color, laser power delivery, tissue properties, photobleaching, and photocreation of compounds for monitoring and feedback control.

Therapies, Surgeries, and Monitoring

Photodynamic Therapy (PDT);

Heating of tissue and/or tumors, (e.g. hyperthermia treatment);

Laser surgery from optical illumination (UV, heat, and/or ablation)

Photoactivated chemistry, photopolymerization, and implantation of biomaterials;

Laser cauterization from hot-tipped scanner (optically or electronically heated); and Mechanical destruction of tissue using shock waves produced by absorption of pulsed optical radiation.

Interactive Displays & Advanced User Interface Design

Quasi-stereo on display monitors, stereographic mapping using pseudo color overlay, and true 3D display formats (Note: Individual display strategies and capabilities depend on the specific application); and Interactive touch/point screen.

FIGS. 9A and 9B illustrate the different functions that can be carried out with the present invention, depending upon the instrumentation that is used. FIG. 9A shows a single scanning waveguide used for imaging, sampling diagnoses, and administering therapy, while in FIG. 9B, the single scanning waveguide is used for 3D imaging, obtaining a tumor biopsy, and monitoring endoscopic surgery. While in both these figures, many of the components are identically provided, it is helpful to recognize that by making small modifications to the components that are used as part of the system, different functionality can be provided. In a system 460 shown in FIG. 9A, an interactive computer workstation 462 enables medical practitioners to control the scanning optical fiber and to execute software algorithms used for imaging, diagnosis (e.g., optical biopsy), and administering therapy. A high resolution color monitor 464 receives signals from a scanning optical fiber 484 that are conveyed over an optical fiber system 488 to a distribution console 472. Optional RGB detectors may be provided if not included internally within the patient's body adjacent to scanning optical fiber 484. An ROI 486 is scanned by the optical fiber to produce the high resolution color images displayed to a user. In a passive display embodiment, two cathode ray tube monitors (CRTs) display images using two different contrast modes to generate the images of the same object (e.g., tissue). For example, the same resonant driven scanning optical fiber may produce both a full-color optical image on one CRT and a grayscale fluorescence image on the other CRT monitor. If the optical properties of the excitation and signal do not overlap, then two or more images may be generated simultaneously. Otherwise, the two images are either captured in a frame sequential method or in alternating line sweeps of the fast resonant scanner. To switch between image contrast modes (full-color optical and fluorescence), the light sources are shuttered or directly turned off-on. Synchronized in time during the modulation of both illumination power and spectral range, the signals from the photon detectors are recorded and displayed as separate images. In this example, having a second fluorescence image of the same ROI, a medical practitioner can find and positively identify small or pre-cancerous lesions that may or may not be visible on a standard white-light image.

It is contemplated that one of the two displays might be a touch screen monitor that enables the medical practitioner to select (draw the outline) of an ROI for laser surgery. Since the image may be moving, the touch screen monitor will require the image to be captured and frozen in time. However, once this ROI is outlined, image segmentation and object recognition algorithms may be implemented to keep the ROI highlighted during real-time image acquisition and display. The touch screen monitor can provide sidebar menus for the practitioner to set parameters for the laser therapies, such as power level and duration of laser radiation exposure. The second display would not provide interactivity, but is preferably a high resolution monitor displaying the real-time optical image in full-color or grayscale. If IR photon detectors are integrated into the endoscope, the high resolution display with pseudo-color will allow the practitioner to monitor the progress of laser therapies, such as tissue heating and/or tissue irradiation in laser surgery.

The scanning optical fiber is positioned at a desired location within the patient's body, opposite ROI 486, using guide wires or a cannula (not shown) and a manual controller that facilitates tip navigation and stabilization, as indicated in a block 466. Within ROI 486, optical biopsy "spots" 485 illustrate the spatial and temporal distribution of single-point spectral measurements to diagnose for disease. These spots are distributed much like the current practice of invasively taking tissue samples for in vitro biopsy analysis. Each spot may be analyzed spectroscopically during a frame cycle of the optical scanner, separating $t_1$ and $t_2$ by, for example, about 1/30 second. In addition to the image provided by the scanning optical fiber, IR thermal photodetectors (and an optional temperature monitor) as indicated in a block 468 could be included for receiving IR signals from the ROI.

To facilitate control of the motion of the scanning optical fiber or light waveguide, electrical power for microsensors and control electronics are provided, as indicated in a block 470. The signals provided by the control electronics enable amplitude and displacement control of the optical fiber when the actuator that causes it to scan is controlled by both electrical hardware and software within block 470. A spectrophotometer and/or spectrum analyzer 474 is included for diagnostic purposes, since the spectral composition of light received from ROI 486 and distribution of optical biopsy locations 485 can be used for screening and diagnosis for such diseases as cancer to a medical practitioner in evaluation of the condition of the ROI, based upon spectral photometric analysis. To illuminate the ROI so that it can be imaged, red, green, and blue light sources 476, 478, and 480 are combined and the light that they produce is conveyed through the optical fiber system to scanning optical fiber 484. The light source used for spectral analysis may be a high power pulse from one of the RGB light sources (e.g., lasers), or a secondary laser or white light source. Since signal strength, time, and illumination intensity are limiting, a repeated single-point spectroscopic method will be initially employed, using flash illumination. In addition, the same or a different high power laser source 482 can be employed to administer therapy, such as PDT, the laser ablation of tumors, and other types of therapy rendered with a high intensity source.

In using system 460, a medical practitioner navigates and maneuvers the flexible single scanning optical fiber component to an appropriate region of a patient's body while watching the high resolution color monitor displaying the standard, full-color endoscopic image. The search for tumors and/or pre-cancerous lesions begins by watching the monitor. A second monitor (not separately shown) included with spectrophotometer and spectrum analyzer 474 displays a fluorescence mapping in pseudo-color over a grayscale version of the endoscopic image. When an ROI is found, such as abnormal appearing tissue, the flexible endoscope is mechanically stabilized (as explained below). The ROI is centered within the FOV, then magnified using the multi-resolution capability provided by the present invention. The size of the ROI or tumor is estimated and a pixel boundary is determined by image processing either the visible image or the fluorescence image. If spectroscopic diagnosis is required, such as LIFS, the distribution of optical biopsy points is estimated along with illumination levels, The diagnostic measurements are performed by delivering the illumination repeatedly over many imaging frames automatically. The user can cease the diagnosis or have the workstation continue to improve signal-to-noise ratio and/or density of sampling until a clear diagnosis can be made. The results of diagnosis is expected to be in real-time and overlaid on top of the standard image.

If optical therapy is warranted, such as PDT, then an optical radiation exposure is determined and programmed into the interactive computer workstation controlling the scanning optical fiber system. The PDT treatment is an optical scan of high intensity laser illumination typically by high power laser source 482, pre-selected for the PDT fluorescent dye, and is controlled using dichroic filters, attenuators, and electromechanical shutters, as explained above. In a frame-sequential manner, both fluorescence images and visible images are acquired during PDT treatment. The medical practitioner monitors the progress of the PDT treatment by observing these acquired images on both displays.

With reference to FIG. 9B, an optical fiber system 460' is used for 3D imaging, biopsy, and monitoring endoscopic surgery. To enable 3D imaging in a quasi-stereo view of the ROI, an HMD 490 is included. In addition, the system includes high resolution color monitor 464, which was described above in connection with FIG. 9A. Also, an IR optical phase detector 492 is included for range finding. High frequency modulation of IR illumination can be measured to determine phase shifts due to optical propagation distances on the order of a few millimeters. The distance between the distal end of the scanning optical fiber or light waveguide and ROI 486 can be important in evaluating the intensity of light that should be applied during endoscopic surgery, for mapping a specific ROI 487 to determine its boundary or size, and for determining the size and shape of features such as a volume of a tumor comprising the ROI. An UV-visible biopsy light source 494 enables an optical biopsy to be carried out at specific ROI 487. The spectrophotometer and spectrum analyzer in block 474 are useful in monitoring the status of the ROI during endoscopic surgery being carried out, since the condition of the ROI during the endoscopic surgery can sometimes best be determined based upon the spectrum analysis provided by this instrumentation. In other respects, the components used for the alternative functions provided in FIG. 9B are identical to those in FIG. 9A.

When using system 460', a medical practitioner again searches for tumors by moving the flexible tip of single scanning optical fiber while watching high resolution color monitor 464 that shows the visible wavelength (full-color) image. When a tumor is found, the scanning optical fiber is mechanically stabilized. Again, the ROI is centered within the FOV, and then magnified with the multi-resolution capability. However, if the surrounding tissue is moving so the acquired image is not stationary, a snapshot of the image is captured and transferred to the interactive computer workstation monitor, which is a touch screen type display. The boundary of the stationary ROI is outlined on the touch screen, and a volume of the tumor is estimated from a diameter measurement in pixels and a distance measurement between the scope and the tissue using IR optical phase detector for range finding 492. An optical biopsy is taken with UV-visible biopsy light source 494, which can be a fiber-coupled arc lamp for elastic scattering spectroscopy (ESS). If warranted for this tumor, the optical radiation exposure is calculated, and a treatment protocol is programmed into interactive computer workstation monitor 462. For maintaining image stabilization, digital image processing algorithms can be calibrated for automatically segmenting this ROI or processing to eliminate motion artifacts from the acquired images in real-time, which may be equivalent or less than the display frame rate. The laser surgical treatment of cauterization can occur with high intensity laser 482 (IR) that is optically coupled with the visible optical sources. If the IR range finding option is not required, but an IR temperature monitor or laser monitor is desired, then the IR source can instead be used for these alternative monitoring functions. In a frame-sequential manner, both the IR and visible images are acquired during the laser surgery and cauterization. The IR image is either a mapping of the back scatter from the laser illumination as it scans the ROI or a thermal image of the ROI, which can be displayed on the interactive computer display as pseudo-color over a grayscale visible image. The medical practitioner monitors the progress of the IR radiation treatment by observing these acquired images on both the high resolution and touch screen display monitors.

Stabilization and Scanning Without a Lens

Since rendering therapy and diagnosis, as well as imaging an ROI requires a relatively stable platform for the scanning optical fiber, it is sometimes important to provide a mechanism for stabilizing the scanning optical fiber within a body passage 510, as shown in FIG. 10. In this view, an optical fiber assembly 500 includes an inflatable balloon 504, which is inflated through a lumen (not shown) included within the optical fiber assembly. By inflating balloon 504 so that it contacts the sides of passage 510, the disposition of optical fiber assembly 500 becomes fixed relative to the passage. An ROI 514 on a wall 512 of the passage can then be imaged. The scanning optical fiber can then image and render diagnostic, therapy, and/or monitoring functions in regard to the ROI without concern that the distal end of the optical fiber assembly may move substantially relative to the ROI. However, this method will not eliminate relative tissue motions, often produced by breathing and blood flow. An electronic method of stabilizing the ROI is to electronically freeze the image on an interactive touch-sensitive display screen, marking the boundary of the ROI on the touch-sensitive screen, and using image segmenting and processing algorithms to record threshold levels of this ROI. By running these algorithms on the acquired images and tracking the ROI, the boundary can be maintained during relative tissue motions for accurate therapeutic applications.

While the embodiments of the scanning optical fiber or light waveguide disclosed above have in each case included either an imaging or a scan lens, it is also possible to construct a scanning optical fiber that does not use either the imaging or scan lenses of these other embodiments. As shown in FIGS. 11A–11C, a scanning waveguide 516 conveys light through optical fiber assembly 501 having a distal transparent glass window 502 so that light emitted by scanning waveguide 516 is directly transmitted through the window and onto wall 512 of the passage. The light thus is directed onto ROI 514. The light emitted by scanning waveguide 516 that has a low angle of divergence or an extended range beam waist 518. As indicated in FIG. 11B, waveguide 516 is caused to scan, either in a linear or 2D fashion such as one of the other modes that enables the light emitted by it to cover all of the surface of ROI 514. Scanning optical fiber 516 includes a single mode optical fiber section 524, to provide high optical quality input, and a multi-mode optical fiber 526 at its distal end, to provide a gradient index of refraction 528, for reduced divergence, better focus, or collimation. Further details of the distal end of scanning waveguide 516 and of transparent glass window 502, are illustrated in FIG. 11C.

Retrofitting a Rigid Endoscope with Scanning Optical Fiber System

It has been recognized that a scanning optical fiber in accord with the present invention can be implemented as a retrofit to existing high resolution rigid endoscope systems, such as an endoscope 540 shown in FIG. 12. As shown in FIG. 12, an optical fiber assembly 542 includes an actuator 544 (piezoelectric, piezoceramic, or other electromechanical device) used to cause the scanning motion of a scanning optical fiber 546. Light emitted by the scanning optical fiber is reflected from a beam splitter 554, which is a dichroic mirror and/or a polarization type device. The light is thus directed through a lens 556 that focuses the light into a relay lens system 558. An objective lens 560 at the distal end of the relay lens system focuses the light onto tissue 562 at the ROI. At a time $t_1$, the light travels through objective lens 560 along a path as indicated by $t_1$, while at a time $t_2=t_1+\Delta t$, the light travels along a different path. Light from the ROI passes through objective lens 560 and relay lens system 558, through lens 556, and through beam splitter 554. The light then is focused by a lens 564 into a charge coupled device (CCD) 566 (or to a video camera). The signal produced by the CCD or video camera is conveyed through a lead 568 externally to enable imaging of the tissue being illuminated. In addition to, or replacing an imaging camera, the illumination light can be combined with diagnostic and/or therapeutic light, which can be imaged or monitored in time-series by separate optical detectors. The imaging, diagnostic, and/or therapeutic light received from the tissue is directed by beam splitter 554 back through a lens 552 and onto photodiodes 548 and/or optical fibers (not shown). The photodiodes produce signals that are conveyed through leads 550 that run through optical fiber assembly 542 to external instrumentation used for processing the light signals. Microsensors 570 that optically track the position of scanning optical fiber 546 provide a signal that enables higher accuracy and speed in delivering the scanned illumination to be achieved by accurately determining the scanning motion (e.g., position, velocity, frequency, etc.) of the scanning optical fiber.

It will be understood that in a conventional rigid endoscope, a ring of optical fibers is typically used for providing a diffuse white light illuminating the ROI. In the retrofit endoscope of FIG. 12, the scanning optical fiber can convey all necessary illumination for imaging, diagnosis, and therapy. Unlike the previous embodiments, the scanning optical fiber in the retrofit endoscope is not disposed at the distal tip of the device and therefore does not suffer from the relatively strict dimensional constraints. In this embodiment, the advantages of the present invention include the ability to direct high energy laser illumination with pixel accuracy, to implement fluorescent imaging and other diagnostic evaluations for cancer screening and other diagnostic purposes, and to carry out range finding. In addition, optical therapies and tissue sensing, and dosage monitoring can be implemented with this system. It is also contemplated that the system can be expanded to the proximal end of a flexible imaging system, but there may then be an unacceptable loss of optical resolution. With the device shown in FIG. 12, photodiodes 548 can be replaced with optical fibers for spectroscopic analysis or made confocal for coherence measurements at the proximal end, as part of the optical diagnosis. Alternatively, a tapered or pulled glass optical fiber or a thin film waveguide could be used rather than the scanning optical fiber illustrated, for high resolution optical scanning.

Although the present invention has been described in connection with the preferred form of practicing it and modifications thereto, those of ordinary skill in the art will understand that many other modifications can be made to the present invention within the scope of the claims that follow. Accordingly, it is not intended that the scope of the invention in any way be limited by the above description, but instead be determined entirely by reference to the claims that follow.

The invention in which an exclusive right is claimed is defined by the following:

1. Apparatus for selectively providing imaging and at least one other function for a region of interest in a patient, comprising:
   (a) at least one light source that produces light;
   (b) a light guide having a proximal end and a distal end, the at least one light source being optically coupled to the proximal end of said light guide, so that light from all of said at least one light source is conveyed along a single optical path defined by the light guide toward a region of interest, said distal end of the light guide being adapted to be positioned adjacent to a region of interest;
   (c) a scanning actuator disposed adjacent to the distal end of the light guide, said scanning actuator driving a distal end of the light guide into a resonance movement mode, causing light produced by the at least one light source that is conveyed through the light guide to scan a region of interest, illuminating only a pixel at a time in regard to an image of a region of interest;
   (d) a light detector that receives light from each pixel that is illuminated by the scanning actuator in a region of interest, producing a signal corresponding to an intensity of said light for use in producing an image of a region of interest;
   (e) a display adapted to enable a user to visualize an image of a region of interest; and
   (f) a control circuit that is coupled to control the scanning actuator, the at least one light source, and the light guide, said control circuit being adapted to selectively energize the at least one light source to image a region of interest and render at least one other function to a region of interest, said at least one other function including at least one of diagnosing a condition, rendering a therapy, sensing a condition, and monitoring a condition.

2. The apparatus of claim 1, wherein the at least one light source comprises a plurality of light sources that emit light of different colors, further comprising a combiner that combines the light of different colors emitted by the plurality of light sources for input to the proximal end of the light guide.

3. The apparatus of claim 2, wherein the light detector comprises a plurality of light sensors that are each sensitive to one of the different colors of light emitted by the plurality of light sources.

4. The apparatus of claim 3, further comprising a polarizing filter adapted to be disposed between at least one of:
   (a) the at least one light source and a region of interest, so that a region of interest is illuminated with a polarized illumination light; and
   (b) the region of interest and at least one light sensor.

5. The apparatus of claim 4, wherein the light detector detects polarized light having a predefined axis of polarization.

6. The apparatus of claim 1, wherein the light detector comprises a plurality of light sensors that are disposed adjacent to the distal end of the optical fiber.

7. The apparatus of claim 6, further comprising a plurality of light guides that convey the light reflected from a region of interest to the plurality of light sensors.

8. The apparatus of claim 7, wherein different portions of the plurality of light guides are adapted to convey light collected from within a region of interest, using light sensors that are spaced apartf from each other, enabling a quasi-stereo image of a region of interest to be visualized by a user with the display.

9. The apparatus of claim 7, wherein different portions of the plurality of light guides are adapted to convey light collected from within a region of interest using light sensors that are spaced-apart from each other, to substantially reduce an effect of specular reflections in an image of the region of interest.

10. The apparatus of claim 1, further comprising a plurality of light guides having proximal ends and distal ends, wherein the light detector comprises a plurality of light sensors that are coupled to the proximal end of the light guides.

11. The apparatus of claim 10, wherein said at least one additional light guide uses at least one of cladding and a concentric region of appropriate refractive index to propagate light through the light guides toward the plurality of light sensors that are coupled to the distal end of the light guides.

12. The apparatus of claim 11, wherein the light guides comprise a concentric optical fiber assembly that conveys light bi-directionally to and from the region of interest.

13. The apparatus of claim 1, wherein the scanning actuator comprises at least one electromechanical actuator that moves the distal end of the light guide in a two-dimensional scanning mode.

14. The apparatus of claim 1, wherein the scanning actuator comprises a piezoceramic actuator that is energized at a harmonic of a resonant frequency of the distal end of the light guide, causing the light guide to oscillate.

15. The apparatus of claim 1, wherein the light guide comprises an optical fiber, and wherein the distal end of the optical fiber is tapered to a substantially smaller cross-sectional size than a more proximal portion of the optical fiber.

16. The apparatus of claim 1, further comprising at least one lens adapted to be disposed between the distal end of the light guide and a region of interest, said at least one lens being adapted to focus the light produced by the at least one light source onto a region of interest.

17. The apparatus of claim 16, wherein said at least one lens comprises a lens mounted at the distal end of the light guide, said scanning actuator being adapted to drive the distal end of the light guide in a resonance mode to scan a region of interest, said lens that is mounted at the distal end of the light guide having sufficient mass so that the lens generally rotates as the light guide moves to change a direction in which light is emitted, when scanning a region of interest.

18. The apparatus of claim 1, wherein the light guide comprises a first thin film optical waveguide disposed at the distal end of the light guide so that the light emitted by the at least one light source passes through the first thin film optical waveguide and is thus adapted to be directed onto a region of interest.

19. The apparatus of claim 18, wherein the scanning actuator is disposed adjacent to the first thin film optical waveguide and moves the first thin film optical waveguide, being thereby adapted to cause the light to scan a region of interest.

20. The apparatus of claim 18, wherein the light guide comprises a second thin film optical waveguide disposed at the distal end of the light guide and moved generally in parallel with the first thin film optical waveguide and thereby adapted to scan a region of interest in parallel with the first thin film optical waveguide.

21. The apparatus of claim 20, wherein one of the first and second thin film optical waveguides images the region of interest, while the other of the first and second thin film optical waveguides renders said at least one other function in regard to the region of interest.

22. The apparatus of claim 18, wherein the thin film optical waveguide has a cross-sectional size less than 0.01 mm.

23. The apparatus of claim 1, wherein the at least one light source is adapted to provide at least one of a visible light, an ultraviolet light, and an infrared light to illuminate a region of interest.

24. The apparatus of claim 23, wherein the light detector is responsive to at least one of a visible light, an ultraviolet light, and an infrared light.

25. The apparatus of claim 1, wherein the light detector is responsive to light emitted from a region of interest due to one of phosphorescence and fluorescence.

26. The apparatus of claim 1, further comprising at least one of a spectrophotometer and a spectrum analyzer coupled to the light detector for use in diagnosing a condition of a region of interest.

27. The apparatus of claim 1, further comprising a thermal detector coupled to one of the proximal and distal ends of the light guide for use in monitoring a temperature in a region of interest.

28. The apparatus of claim 1, wherein the display comprises a stereo display that enables a user to visualize a quasi-stereo image of a region of interest.

29. The apparatus of claim 1, further comprising means for guiding and maneuvering the distal end of the light guide to a region of interest within a patient.

30. The apparatus of claim 1, further comprising a balloon disposed adjacent to the distal end of the light guide, said balloon being adapted to stabilize the distal end of the light guide in a cavity within a patient when the balloon is inflated.

31. The apparatus of claim 1, further comprising electrical leads that extend along the light guide, to its distal end, said electrical leads being connected to the scanning actuator to energize it.

32. The apparatus of claim 1, further comprising sensors that monitor movement of the distal end of the light guide and which are coupled to the control circuit to enable the scanning actuator to be controlled when scanning the region of interest.

33. A method for using an integral light guide system to selectively image and carry out at least one other substantive function in connection with a region of interest in a patient, said method comprising the steps of:
  (a) directing a light at the region of interest in the patient through a light guide;
  (b) scanning the region of interest with the light by moving the light guide, wherein the step of scanning comprises the step of driving a distal end of the light guide into a resonance movement mode, so that the region of interest is illuminated with the light a pixel at a time, in regard to an image of the region of interest;
  (c) detecting light from the region of interest and in response thereto, producing signals indicative of characteristics of said light, including an intensity of the light received from the region of interest;
  (d) imaging the region of interest, using the signals produced by the step of detecting; and
  (e) controlling the administration of the light to the region of interest through the light guide, to selectively carry out at least one of the steps of:
    (i) monitoring the region of interest;
    (ii) determining a biophysical condition of the region of interest; and
    (iii) rendering therapy to the region of interest with the light directed thereon.

34. The method of claim 33, further comprising the step of receiving light from the region of interest at a plurality of spaced-apart locations, said step of imaging comprising the step of enabling a user to visually perceive a quasi-stereo image of the region of interest.

35. The method of claim 34, further comprising the step of substantially reducing an effect of specular reflection from the region of interest, using the light received from the plurality of spaced-apart locations.

36. The method of claim 33, wherein the step of scanning comprises the step of causing the light guide to move so that the light emitted from the light guide scans over the region of interest in two generally orthogonal directions.

37. The method of claim 33, wherein the step of scanning comprises the step of causing the light guide to move so that the light emitted from the light guide scans over the region of interest in a helical arc.

38. The method of claim 33, wherein the step of scanning comprises the step of causing the light guide to move so that the light emitted from the light guide scans the region of interest in at least one of:
  (a) generally concentric circles of different radii; and
  (b) a propeller scan mode.

39. The method of claim 33, further comprising the step of focusing the light onto the region of interest through a lens.

40. The method of claim 39, further comprising the step of mounting the lens at a distal end of the light guide.

41. The method of claim 40, wherein the lens is of sufficient mass that as the light guide moves, the lens is rotated about a center of the lens, but otherwise remains generally fixed.

42. The method of claim 33, wherein a distal end of the light guide comprises a thin film optical waveguide, said step of scanning comprising the step of causing the thin film optical waveguide to move so that light emitted thereby is scanned over the region of interest.

43. The method of claim 33, wherein the light directed to the region of interest comprises a high intensity laser light that is directed at undesired tissue on the region of interest to cause the undesired tissue to be destroyed.

44. The method of claim 33, further comprising the step of selectively screening the region of interest to detect any pathological condition associated with the region of interest.

45. The method of claim 33, further comprising the step of selectively sensing a natural biological state of the region of interest to detect a pathological condition.

46. The method of claim 33, wherein the step of determining comprises the step of identifying any pathological condition of the tissue by detecting at least one of:
  (a) a spectrum of light scattered by tissue in the region of interest;
  (b) a spectrum of light emitted by tissue in the region of interest; and
  (c) a spectrum of light absorbed by tissue in the region of interest.

47. The method of claim 33, wherein the light directed at the region of interest comprises light in a predefined waveband, and wherein the step of determining comprises the step of detecting an absorption spectrum of tissue in the region of interest when exposed to the light in the predefined waveband, to identify any pathological condition of the tissue.

48. The method of claim 47, wherein the step of detecting the absorption spectrum includes the step of mapping at least one of an absorption ratio, an emitted fluorescence ratio, and a phosphorescence ratio for the tissue to identify any pathological condition of the tissue.

49. The method of claim 33, wherein the step of rendering therapy comprises the step of delivering the light to the region of interest with a pixel-by-pixel resolution based upon the image of the region of interest.

50. The method of claim 33, further comprising the step of using light to render therapy to the region of interest and to monitor a condition of the region of interest as a result of rendering therapy thereto.

51. The method of claim 33, further comprising the step of endoscopically advancing a distal end of the light guide to the region of interest in the patient.

52. The method of claim 33, wherein the step of imaging the region of interest includes the step of more definitively determining a boundary of the region of interest.

53. The method of claim 33, wherein the step of determining comprises the step of performing an optical coherence tomography and reflectometry analysis of the region of interest.

54. The method of claim 33, wherein the step of determining comprises the step of performing at least one of a laser induced fluorescence analysis, a fluorescence lifetime analysis, an elastic scattering spectroscopy analysis, an optically stimulated vibro-acoustography analysis, a Raman spectroscopy analysis, and detecting chemi-luminescence, of the region of interest.

55. The method of claim 33, further comprising the step of carrying out steps (a)–(e) using a plurality of integral light guides arranged in an array.

56. The method of claim 33, further comprising the step of retrofitting an existing rigid endoscope system with the integral light guide system prior to the step of scanning the region of interest.

57. The method of claim 33, further comprising the step of retrofitting at least one of an existing semi-flexible relay system formed as a rod and a flexible optical fiber with the integral light guide system prior to the step of scanning the region of interest.

58. The method of claim 33, further comprising the step of illuminating and imaging the region of interest while simultaneously rendering said at least one other substantive function.

59. The method of claim 33, further comprising the step of imaging the region of interest in a frame-sequential manner.

60. The method of claim 33, further comprising the step of employing a frame sequence for alternately:

(a) imaging the region of interest during one frame of the frame sequence; and (b) rendering said at least one other substantive function to the region of interest in a next frame of the frame sequence.

61. The method of claim 33, further comprising the step of enabling a user to employ a touch-sensitive display in controlling the integral light guide system.

62. The method of claim 33, further comprising the step of employing an audio enhancement to convey information to a user during the step of scanning of the region of interest.

63. The method of claim 33, wherein the step of imaging the region of interest comprises the step of enabling a user to visualize the region of interest as a quasi-stereo image on a stereo display.

64. The method of claim 33, further comprising the step of stabilizing the integral light guide system during the step of scanning.

65. The method of claim 33, further comprising the step of electronically stabilizing the region of interest during the step of imaging.

66. The method of claim 65, wherein the step of electronically stabilizing comprises the step of freezing an image of the region of interest on a display, and processing the signals produced by scanning to maintain a boundary of the region of interest stable on the display.

67. The method of claim 33, wherein the step of imaging includes the step of zooming an image in real-time.

68. The method of claim 33, further comprising the step of changing a resolution and a field of view dynamically, to enable zooming and dynamic magnification of the field of view when imaging the region of interest.

69. Apparatus for automatically scanning a region of interest within a patient's body, comprising:

(a) a light source;

(b) a light guide that is optically coupled to the light source and having a proximal end and a distal end, said light guide being adapted to convey light emitted by the light source from the proximal end of the light guide along a single light path to a region of interest within a patient's body; and (c) a scanning actuator that is disposed adjacent to the distal end of the light guide, said scanning actuator being coupled to the light guide and adapted to cause the distal end of the light guide to move about so that light conveyed through the light guide produces a scanning pattern on a region of interest, illuminating a region of interest a pixel at a time.

70. The apparatus of claim 69, wherein the scanning actuator comprises a pair of electromechanical actuators that respectively move the distal end of the light guide in substantially transverse directions.

71. The apparatus of claim 69, wherein the scanning actuator comprises a piezoceramic actuator that is energized at a harmonic of a resonant frequency of the distal end of the light guide, causing the light guide to oscillate.

72. The apparatus of claim 69, wherein the light guide comprises an optical fiber, and wherein the distal end of the optical fiber is tapered to a substantially smaller cross-sectional size than a more proximal portion of the optical fiber.

73. The apparatus of claim 69, further comprising at least one lens adapted to be disposed between the distal end of the light guide and a region of interest, said at least one lens being adapted to focus the light produced by the at least one light source onto a region of interest.

74. The apparatus of claim 73, wherein said at least one lens comprises a lens mounted at the distal end of the light guide, said scanning actuator being adapted to drive the distal end of the light guide in a resonance mode to scan a region of interest, said lens that is mounted at the distal end of the light guide having sufficient mass so that the lens generally rotates as the light guide moves to change a direction in which light is emitted, when scanning a region of interest.

75. The apparatus of claim 69, wherein the light guide comprises a thin film optical waveguide disposed at the distal end of the light guide so that the light conveyed through the light guide passes through the thin film optical waveguide and is thus adapted to be directed onto a region of interest.

76. The apparatus of claim 75, wherein the scanning actuator is disposed adjacent to the thin film optical waveguide and moves the thin film optical waveguide in the scanning pattern.

77. The apparatus of claim 75, wherein the thin film optical waveguide has a cross-sectional size less than 0.01 mm.

78. The apparatus of claim 69, further comprising a light detector adapted to receive light from the region of interest.

79. A method for automatically scanning a region of interest in a patient's body, comprising the steps of:
  (a) conveying light from a source along a single path through a light guide having a distal end that is disposed adjacent to the region of interest;
  (b) automatically moving the distal end of the light guide in a desired scanning pattern in response to a scanning signal; and
  (c) scanning the region of interest with light directed at the region of interest through the distal end of the light, directing the light at the region of interest in said scanning pattern, to illuminate the region of interest a pixel at a time, wherein the step of scanning comprises the step of driving a distal end of the light guide into a resonance movement mode.

80. The method of claim 79, wherein the step of scanning comprises the step of causing the distal end of the light guide to move so that the light emitted from the light guide scans over the region of interest in two generally orthogonal directions.

81. The method of claim 79, wherein the step of scanning comprises the step of causing the light guide to move so that the light emitted from the light guide scans over the region of interest in a helical arc.

82. The method of claim 79, wherein the step of scanning comprises the step of causing the light guide to move so that the light emitted from the light guide scans the region of interest in one of:
  (a) generally concentric circles of different radii; and
  (b) a propeller scan mode.

83. The method of claim 79, further comprising the step of mounting a lens at a distal end of the light guide.

84. The method of claim 83, wherein the lens is of sufficient mass that as the light guide moves, the lens is rotated.

85. The method of claim 79, wherein a distal end of the light guide comprises a thin film optical waveguide, said step of scanning comprising the step of causing a distal end of the thin film optical waveguide to move so that light emitted thereby is scanned over the region of interest in the desired scanning pattern.

86. The method of claim 79, wherein the step of scanning comprises the step of driving a distal end of the light guide into a resonance movement mode.

87. The method of claim 79, further comprising the step of detecting light from the region of interest to produce a signal used for imaging the region of interest.

\* \* \* \* \*